US009669152B2

(12) United States Patent
Kimura et al.

(10) Patent No.: US 9,669,152 B2
(45) Date of Patent: *Jun. 6, 2017

(54) METHOD AND APPARATUS FOR SEPARATING BLOOD COMPONENTS INCLUDING RE-PROCESSING A LOW-CONCENTRATION BLOOD COMPONENT

(71) Applicant: TERUMO KABUSHIKI KAISHA, Tokyo (JP)

(72) Inventors: Shigeyuki Kimura, Shizuoka (JP); Ryoji Kataoka, Lakewood, CO (US)

(73) Assignee: Terumo Kabushiki Kaisha, Tokyo (JP)

( * ) Notice: Subject to any disclaimer, the term of this patent is extended or adjusted under 35 U.S.C. 154(b) by 106 days.

This patent is subject to a terminal disclaimer.

(21) Appl. No.: 14/497,839

(22) Filed: Sep. 26, 2014

(65) Prior Publication Data

US 2015/0011371 A1    Jan. 8, 2015

Related U.S. Application Data

(63) Continuation of application No. PCT/JP2013/054760, filed on Feb. 25, 2013.

(30) Foreign Application Priority Data

Mar. 27, 2012 (JP) ................... 2012-072513

(51) Int. Cl.
*A61M 1/36*    (2006.01)
*A61M 1/38*    (2006.01)
(Continued)

(52) U.S. Cl.
CPC ........ *A61M 1/3693* (2013.01); *A61M 1/3696* (2014.02); *A61M 1/382* (2013.01);
(Continued)

(58) Field of Classification Search
CPC .............. A61M 1/3696; A61M 1/0231; A61M 1/0218; A61M 1/3693; A61M 1/382;
(Continued)

(56) References Cited

U.S. PATENT DOCUMENTS

| 3,565,330 A | 2/1971 | Latham, Jr. |
| 4,753,729 A | 6/1988 | Schoendorfer et al. |

(Continued)

FOREIGN PATENT DOCUMENTS

| JP | 2003516175 A | 5/2003 |
| JP | 2005296675 A * | 10/2005 |

(Continued)

OTHER PUBLICATIONS

JP 2005296675 Description Epacenet Machine Translation.*

(Continued)

*Primary Examiner* — Charles Cooley
*Assistant Examiner* — Shirley S Liu
(74) *Attorney, Agent, or Firm* — John R. Merkling

(57) ABSTRACT

Provided is a blood component separation device that can shorten the overall time to collect high-concentration platelet liquid for blood component donation, thereby reducing time to keep a donor for blood drawing. The blood component separation device includes a temporary storage bag (also used as a buffy coat bag) which is also used as a whole blood bag for storing whole blood drawn from the donor. A control means performs whole blood drawing from the donor in parallel with performing at least either of a circulation flow step and an acceleration step, thereby storing the collected whole blood in the temporary storage bag.

3 Claims, 19 Drawing Sheets

(51) Int. Cl.
*A61M 1/02* (2006.01)
*B04B 13/00* (2006.01)
*B04B 11/04* (2006.01)

(52) U.S. Cl.
CPC ........... *B04B 13/00* (2013.01); *A61M 1/0218* (2014.02); *A61M 1/0231* (2014.02); *A61M 2202/0427* (2013.01); *A61M 2205/33* (2013.01); *A61M 2205/331* (2013.01); *A61M 2205/42* (2013.01); *B04B 11/04* (2013.01)

(58) Field of Classification Search
CPC .. A61M 2202/0427; A61M 2202/0413; A61M 2205/33; A61M 2205/331; A61M 2205/42; B04B 1/02; B04B 11/00; B04B 11/04; B04B 13/00
USPC .................................................. 494/37, 42, 6
See application file for complete search history.

(56) References Cited

U.S. PATENT DOCUMENTS

| | | | |
|---|---|---|---|
| 5,939,319 | A | 8/1999 | Hlavinka et al. |
| 7,413,665 | B2 | 8/2008 | Holmes et al. |
| 2002/0062100 | A1* | 5/2002 | Pierce ..................... A61M 1/02 604/6.01 |
| 2004/0195190 | A1 | 10/2004 | Min et al. |
| 2009/0259162 | A1 | 10/2009 | Ohashi et al. |
| 2009/0309308 | A1 | 12/2009 | Jorgensen et al. |
| 2016/0317727 | A1* | 11/2016 | Hirabuki ............. A61M 1/3693 |

FOREIGN PATENT DOCUMENTS

| | | |
|---|---|---|
| JP | 3850429 B2 | 11/2006 |
| JP | 2009226210 A * | 10/2009 |
| WO | WO01/28621 A1 | 4/2001 |

OTHER PUBLICATIONS

JP 2009226210 Machine Translation filed by applicant on Oct. 22, 2014.*
International Search report for PCT Application No. PCT/JP2013/054760, issued by the Japanese Patent Office on Apr. 9, 2013.
European Extended Search Report for European Application No. 13761915.1, issued by the European Patent Office on Oct. 16, 2015.
European Extended Search Report for European Application No. 13767918.9, issued by the European Patent Office on Oct. 16, 2015.

* cited by examiner

METHOD AND APPARATUS FOR SEPARATING BLOOD COMPONENTS INCLUDING RE-PROCESSING A LOW-CONCENTRATION BLOOD COMPONENT

TECHNICAL FIELD

The present invention relates to a blood component separation device including a centrifugal separator for separating a predetermined blood component from blood and a container for containing the predetermined blood component which is centrifugally separated.

Conventionally, in the field of blood drawing, a blood component such as platelets is collected by collecting only the component from drawn blood and returning the remaining blood components into the donor. In such operation, a blood component separation device including a centrifugal separator is used.

In recent years, in the field of radiation therapy of cancer or the like, transfusion of platelet liquid is widely performed, and high-concentration platelet liquid is necessary. To obtain high-concentration platelet liquid, Patent Literature 1 discloses an art using a blood component separation device to temporarily store low-concentration platelet liquid in a buffy coat bag and store only high-concentration platelet liquid in a platelet intermediate bag. That is, low-concentration platelet liquid flows out first from the centrifugal separator, then high-concentration platelet liquid, and finally low-concentration platelet liquid again. When the first portion and the last portion of the platelet liquid, which has low-concentration of platelets, are stored in the platelet intermediate bag, the concentration of the platelet liquid stored in the platelet intermediate bag will naturally be reduced. To avoid that, the low-concentration platelet liquid, that is, the first portion and the last portion of the platelet liquid, is temporarily stored in the buffy coat bag. In the second cycle, the stored platelet liquid is mixed with the whole blood drawn from a donor and supplied to the centrifugal separator. By repeating this process, only high-concentration platelet liquid can be stored in the platelet intermediate bag.

CITATION LIST

Patent Literatures

Patent Literature 1: JP 3850429 B1
Patent Literature 2: JP 2009-226210 A

SUMMARY OF INVENTION

Technical Problem

The technique disclosed in Patent Literature 1 however has disadvantage as described below.

In a blood component donation, an amount of high-concentration platelet liquid collected in a cycle is as little as 10 ml, requiring three to four cycles of drawing to collect a predetermined amount of high-concentration platelet liquid. This keeps a blood donor for a long time, which causes great inconvenience to a busy donor. Moreover, a donor preferring a blood component donation might have no choice for blood component donation but for whole blood donation if the donor is busy.

The present invention is made in view of such issue. The object of the present invention is to provide a blood component separation device that can shorten the overall time to collect whole blood for collecting high-concentration platelet liquid for blood component donation, thereby reducing time to keep a donor for blood drawing.

Solution to Problem

To achieve the object, a blood component separation device according to an aspect of the present invention is configured as described below.

(1) The blood component separation device includes a centrifugal separator for separating a predetermined blood component from blood and a container for containing the predetermined blood component which is centrifugally separated. The blood component separation device is configured to perform (a) centrifugal separation step for introducing whole blood drawn from a donor into the centrifugal separator to separate the whole blood into a plurality of blood components, (b) circulation flow step for introducing a predetermined first blood component, among centrifugally separated blood components, into the centrifugal separator together with whole blood, and (c) circulation/acceleration step, performed after a predetermined amount of the first blood component is separated in the circulation flow step, in which the supply of whole blood to the centrifugal separator is stopped to introduce only the first blood component into the centrifugal separator to further circulate the first blood component for a predetermined period of time, and a circulation speed is then increased so that a second blood component is separated by the centrifugal separator to be collected. The blood component separation device is characterized in that the whole blood collected from the donor is temporarily stored in a temporary storage container during at least a time period in the circulation/acceleration step. (2) The blood component separation device described in (1) is preferably configured to perform (d) blood returning step for returning blood components, remaining after collecting a predetermined amount of the second blood component in the circulation/acceleration step, to the donor. The blood component separation device is characterized in that the whole blood stored in the temporary storage container is introduced in the centrifugal separator in the centrifugal separation step in a following cycle together with the whole blood collected in the following cycle, where the steps (a) to (d) constitute one cycle. This allows drawing whole blood from the donor in parallel with performing circulation/acceleration step in a first cycle (present cycle). Therefore, the time required to draw whole blood in the second cycle (following cycle) can be reduced, thereby reducing the time required for the entire process. This reduces the time in which the donor receives stress.

For example, typical time periods in each cycle are about 12 minutes for the blood drawing (centrifugal separation step+critical flow step), about 30 to 40 seconds for the circulation step in the circulation/acceleration step, about 20 to 30 seconds for the acceleration step in the circulation/acceleration step, and about 5 minutes for the blood returning. According to the present invention, since blood is previously drawn for one minute in the first cycle, the time required to draw blood in the second cycle can be reduced by one minute, that is, to about 11 minutes. Similarly, when total three cycles are performed, the time required to draw blood in the third cycle can be reduced by one minute, that is, to about 11 minutes.

There is a problem for a donor that the amount of blood circulating outside the body increases, although it may not be a problem for 90% of donors. If there is a problem in increasing the amount of blood circulating outside the body according to the result of previous check, a switching unit may be used to avoid drawing whole blood in parallel with the circulation/acceleration step in the first cycle (present cycle), and to draw whole blood in the second cycle (following cycle) after returning blood.

It goes without saying that, in the last cycle, whole blood is not drawn for the following cycle because there is no cycle following the last cycle.

(3) In the blood component separation device according to (1) or (2), the circulation/acceleration step preferably includes a first collecting step for transferring a low-concentration portion of the second blood component to the temporary storage container and a second collecting step for collecting a high-concentration portion of the second blood component. The blood component separation device is characterized in that the low-concentration second blood component transferred to the temporary storage container is introduced into the centrifugal separator together with the whole blood collected in the temporary storage container in the following cycle and the whole blood drawn in the following cycle. Thus, the blood component separation device can be applied to a BC cycle for obtaining high-concentration platelet liquid allowing drawing whole blood from the donor in parallel with performing the circulation/acceleration step in the first cycle (present cycle). This reduces the time required for drawing whole blood in the second cycle (following cycle) and the time required for the entire process, thereby reducing the time to keep the donor for blood drawing.

(4) The blood component separation device according to (1) or (2) preferably includes a pump for introducing at least either of the whole blood and the low-concentration second blood component contained in the temporary storage container in the preceding cycle into the centrifugal separator in the centrifugal separation step in the following cycle. Therefore, at least either of the whole blood and the low-concentration second blood component contained in the preceding cycle can quickly and surely be introduced into the centrifugal separator.

(5) The blood component separation device according to (3) preferably includes a second storage container for temporarily storing the low-concentration second blood component in the circulation/acceleration step. The blood component separation device is characterized in that the second storage container is also used as the temporary storage container, so that there is no need to additionally provide a second storage container which makes the apparatus large nor to prepare a disposable second storage container, thereby reducing cost.

DESCRIPTION OF EMBODIMENTS

Figure 1:
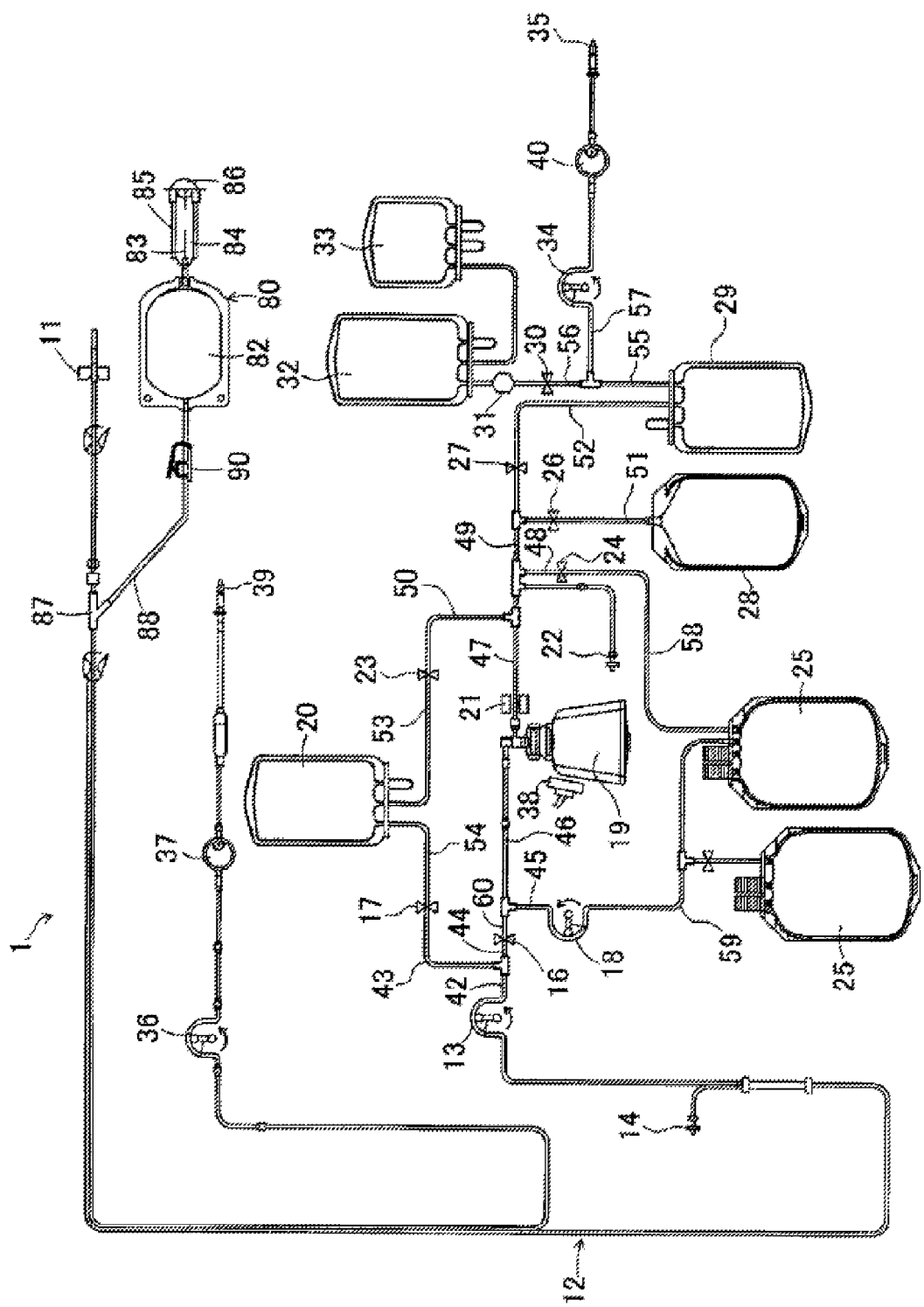
FIG. 1 illustrates a configuration of a blood component separation device according to an embodiment of the present invention.
Figure 19:
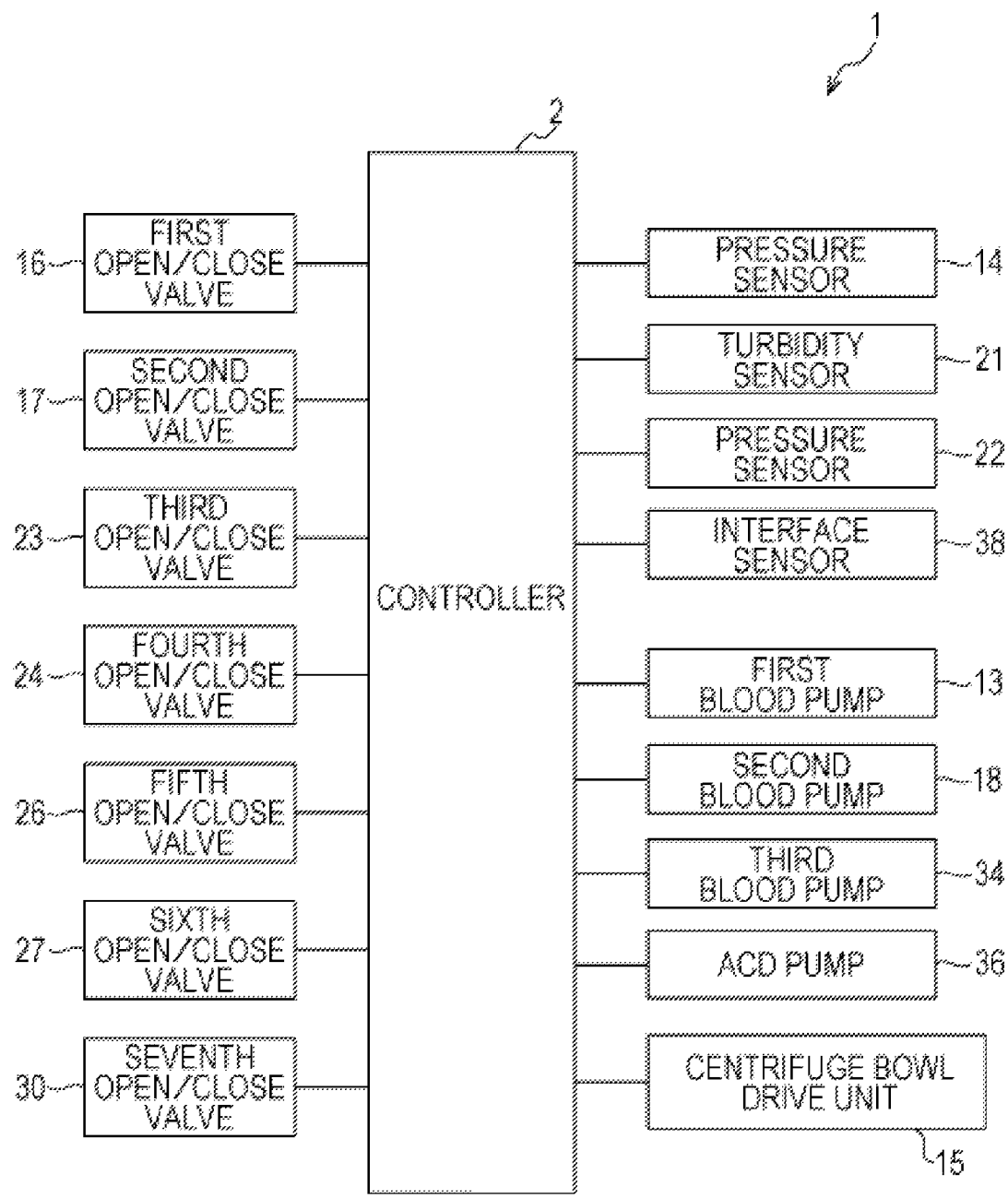
FIG. 19 is a block diagram illustrating a control system of the blood component separation device according to the embodiment.

A system configuration of a blood component separation device according to a first embodiment of the present invention will be illustrated in FIG. 1. FIG. 19 is a block diagram illustrating a control system of the blood component separation device according to the embodiment.

Figure 2:
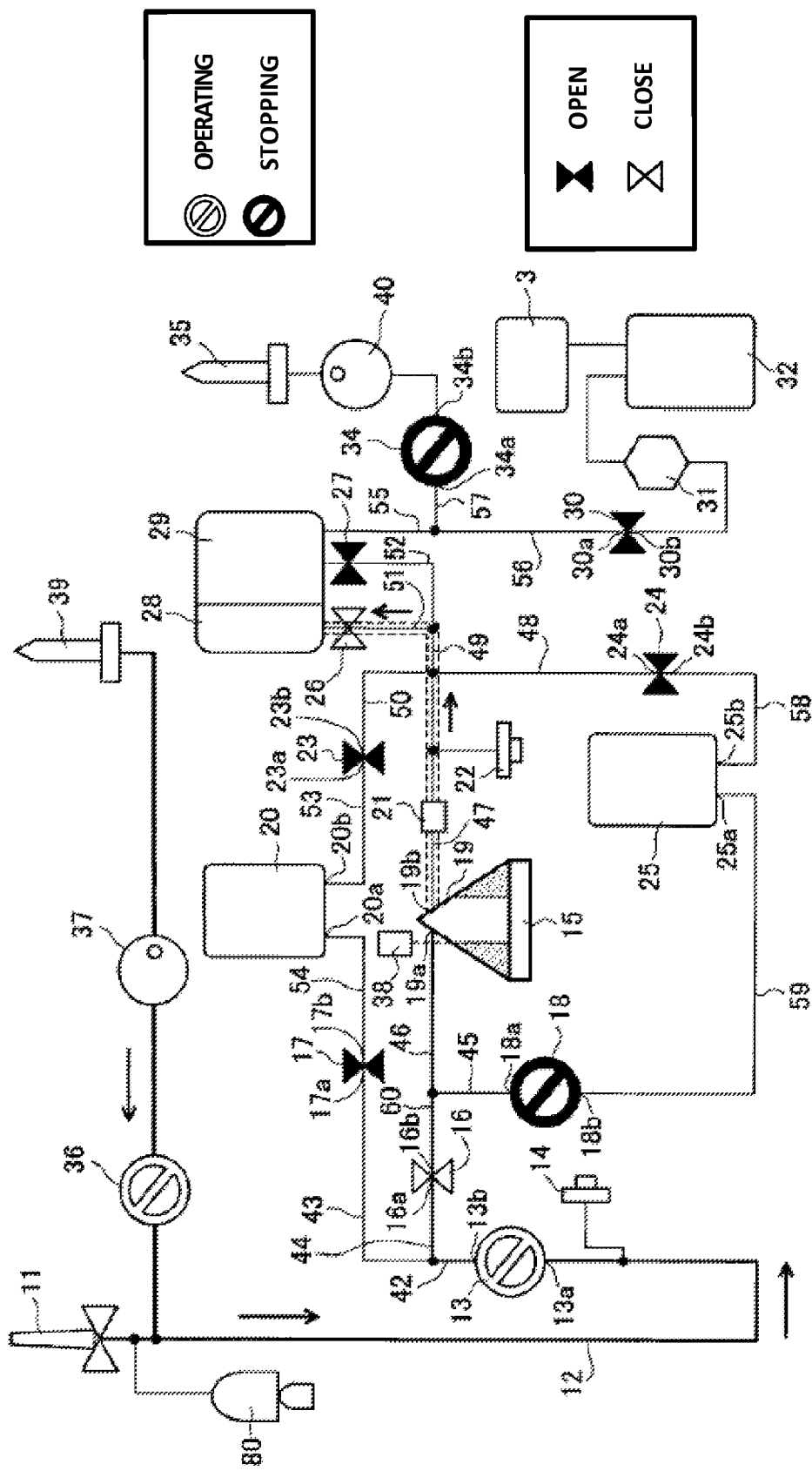
FIG. 2 illustrates a first step (priming step) of the blood component separation device according to the embodiment.

A blood component separation device according to the embodiment includes a blood component separation circuit 1. The blood component separation circuit 1 includes a blood drawing needle 11, an initial blood flow collecting circuit 80 configured with an initial blood flow collecting bag 82 for collecting initial blood flow, a sampling port 85, and an initial blood flow collecting line 88. The blood component separation circuit 1 further includes a centrifuge bowl 19 having therein a space for storing blood. The centrifuge bowl 19 includes a rotor (not shown in the drawing) gripping the centrifuge bowl 19 to rotate, a centrifuge bowl drive unit 15 for rotatably driving the rotor (see FIG. 2), an inflow port (first port 19a), and an outflow port (second port 19b), and is configured to separate blood into a plurality of blood components by the rotation of the rotor. The blood component separation circuit 1 includes three containers for storing blood components separated by the centrifuge bowl 19, that is, a first container (plasma bag) 25, a second container (temporary storage bag) 20, and a third container (platelet intermediate bag) 29. Further, the blood component separation circuit 1 includes a first line, a second line, a third line, a fourth line, a fifth line, and a sixth line. The first line couples the blood drawing needle 11 to the centrifuge bowl 19 and is configured with a donor tube 12, a first blood pump 13, a tube 42, a tube 44, a first open/close valve 16, a tube 60, and a tube 46. The second line couples the centrifuge bowl 19 to the first container 25 and is configured with a tube 47, a tube 48, a fourth open/close valve 24, and a tube 58. The third line couples the first container 25 to the first line and is configured with a tube 59, a second blood pump 18, and a tube 45. The fourth line couples the centrifuge bowl 19 to the second container 20 and is configured with a tube 47, a tube 50, a third open/close valve 23, and a tube 53. The fifth line couples the second container 20 to the first line and is configured with a tube 54, a second open/close valve 17, and a tube 43. The sixth line couples the centrifuge bowl 19 to the third container 29 and is configured with a tube 47, a tube 49, a tube 52, and a sixth open/close valve 27. Note that, two plasma bags 25 are illustrated in FIG. 1, though one of the bags is omitted in FIGS. 2 to 13. Further, the first port and the second port or the input port and the output port of each component are illustrated in FIG. 2.

The blood drawing needle 11, which is a collecting unit to collect whole blood (blood) from a donor, is coupled to a first port 13a of the first blood pump 13 via the donor tube 12. The initial blood flow collecting bag 82 is coupled to the blood drawing needle 11 via a branch 87 provided on the donor tube 12 and the initial blood flow collecting line 88. Further, the initial blood flow collecting bag 82 includes a sampling port 85 for transferring collected initial blood flow to a test container (not shown). The sampling port 85 is constituted with a needle 83, a main body 86, and a cover 84 for covering the needle 83. Further, a klemme 90 is provided on the initial blood flow collecting line 88 to open/close the line. The tube 42 coupled to a second port 13b of the first blood pump 13 is branched into two tubes 43 and 44. The tube 44 is coupled to a first port 16a of the first open/close valve 16. The tube 60 coupled to a second port 16b of the first open/close valve 16 is branched into two tubes 45 and 46. The tube 46 is coupled to the first inflow port 19a of the centrifuge bowl 19 which is a centrifugal separator for separating the drawn blood into a plurality of blood components. The centrifuge bowl 19 is arranged on the centrifuge bowl drive unit 15 (see FIG. 2) to be rotatably driven. The blood drawing needle 11 and the first inflow port 19a, which is an inlet to the centrifuge bowl 19, are coupled via the first line (the donor tube 12, the first blood pump 13, the tube 42, the tube 44, the first open/close valve 16, the tube 60, and the tube 46).

A pressure sensor 14 is coupled to the donor tube 12.

The tube 47 coupled to the second port 19b of the centrifuge bowl 19 is branched into three tubes 48, 49 and 50. The tube 48 is coupled to an input port 24a of the fourth open/close valve 24. An output port 24b of the fourth open/close valve 24 is coupled to an input port 25b of the plasma bag (first container) 25 via the tube 58.

The second port 19b, which is an outlet from the centrifuge bowl 19, and the plasma bag 25 are coupled via the second line (the tube 47, the tube 48, the fourth open/close valve 24, and the tube 58). An output port 25a of the plasma bag 25 is coupled to an input port 18b of the second blood pump 18 via the tube 59. The plasma bag 25 is coupled to the tube 60, constituting the first line, via the tube 45. That is, the plasma bag 25 and the first line are coupled via the third line (the tube 59, the second blood pump 18, and the tube 45). In this manner, the plasma bag 25 is coupled so as to selectively communicate with the inlet to or the outlet from the centrifuge bowl 19.

The tube 50 branched from the tube 47 is coupled to a second port 23b of the third open/close valve 23. A first port 23a of the third open/close valve 23 is coupled to a second port 20b of the temporary storage bag 20 via the tube 53.

That is, the second port 19b of the centrifuge bowl 19 and the temporary storage bag 20 are coupled via the fourth line (the tube 47, the tube 50, the third open/close valve 23, and the tube 53).

A first port 20a of the temporary storage bag 20 is coupled to a second port 17b of the second open/close valve 17 via the tube 54. A first port 17a of the second open/close valve 17 is coupled to the tube 42 via the tube 43.

That is, the temporary storage bag 20 and the tube 42 are coupled via the fifth line (the tube 43, the second open/close valve 17, and the tube 54). In this manner, the temporary storage bag 20 is coupled so as to selectively communicate with the inlet to or the outlet from the centrifuge bowl 19.

The tube 49 is further branched into tubes 51 and 52. The tube 51 is coupled to the air bag 28 via the fifth open/close valve 26, and the tube 52 is coupled to the platelet intermediate bag (third container) 29 via the sixth open/close valve 27.

That is, the second port 19b of the centrifuge bowl 19 and the platelet intermediate bag 29 are coupled via the sixth line (the tube 47, the tube 49, the tube 52, and the sixth open/close valve 27). In this manner, the platelet intermediate bag 29 is coupled to the outlet from the centrifuge bowl 19.

A turbidity sensor 21 for detecting concentration of platelets PLT and a pressure sensor 22 are attached to the tube 47 coupled to the second port 19b of the centrifuge bowl 19. The turbidity sensor 21 detects the turbidity, made by platelets PLT, of plasma PPP flowing in the tube 47.

In the peripheral region of where the centrifuge bowl 19 is attached, an interface sensor 38 for detecting the location of the interface of buffy coat layer BC (see FIG. 14) formed in the centrifuge bowl 19 is provided.

The tube 55 coupled to the platelet intermediate bag 29 is branched into two tubes 56 and 57. The tube 56 is coupled to an inlet port 30a of the seventh open/close valve 30, and the tube 57 is coupled to an outlet port 34a of the third blood pump 34.

An inlet port 34b of the third blood pump 34 is coupled to a platelet reserve liquid bottle (not shown) via a sterilizing filter 40 and a bottle needle 35. An outlet port 30b of the seventh open/close valve 30 is coupled to the platelet bag 32 via a white blood cell removal filter 31. Further, an air bag 33 is coupled to the platelet bag 32.

An output port of an ACD pump 36 is coupled to the donor tube 12. An input port of the ACD pump 36 is coupled to an output port of the sterilizing filter 37. An input port of the sterilizing filter 37 is coupled to an ACD storing bottle (not shown) via a bottle needle 39.

As illustrated in FIG. 19, a controller 2 is configured with, for example, a microcomputer. The controller 2 is electrically coupled to the first blood pump 13, the second blood pump 18, the third blood pump 34, the centrifuge bowl drive unit 15, the ACD pump 36, the turbidity sensor 21, the interface sensor 38, the pressure sensor 14, the pressure sensor 22, the first open/close valve 16, the second open/close valve 17, the third open/close valve 23, the fourth open/close valve 24, the fifth open/close valve 26, the sixth open/close valve 27, and the seventh open/close valve 30.

Detection signals from the sensors 14, 21, 22, and 38 are input to the controller 2 as required. Based on these detection signals or the like, the controller 2 operates or stops the pumps 13, 18, 34, and 36 and controls rotational directions (normal rotation/reverse rotation) and rotational speeds of the pumps. The controller 2 also opens or closes the open/close valves 16, 17, 23, 24, 26, 27, and 30 or controls the operation of the centrifuge bowl drive unit 15 as required.

As a material of the tubes, for example, thermoplastic elastomers such as polyvinyl chloride, polyethylene, polypropylene, polyester such as PET and PBT, ethylene-vinyl acetate copolymer (EVA), polyurethane, and polyester elastomer may be used. Among these materials, particularly, polyvinyl chloride is preferably used. Polyvinyl chloride not only has sufficient ductility and flexibility but also is easy to handle and suitable to be choked by a klemme or the like.

As a material of the bags, soft polyvinyl chloride including DEHP as a plasticizer or products of polymerization or copolymerization of such olefins or diolefins as polyolefin, ethylene, propylene, butadiene, and isoprene can be used. Typical examples include ethylene-vinyl acetate copolymer (EVA), polymer blends formed between EVA and various thermoplastic elastomers, and arbitrary combinations thereof. Further, PET, PBT, PCGT, or the like can be used. Among these materials, particularly, polyvinyl chloride is preferably used. Such material having high gas permeability is preferable for a container for storing platelets PLT to improve shelf life of platelets PLT. Therefore, polyolefin or DnDp-plasticized polyvinyl chloride may preferably be used for such material or a material formed in a thin sheet may preferably be used.

Figure 14:
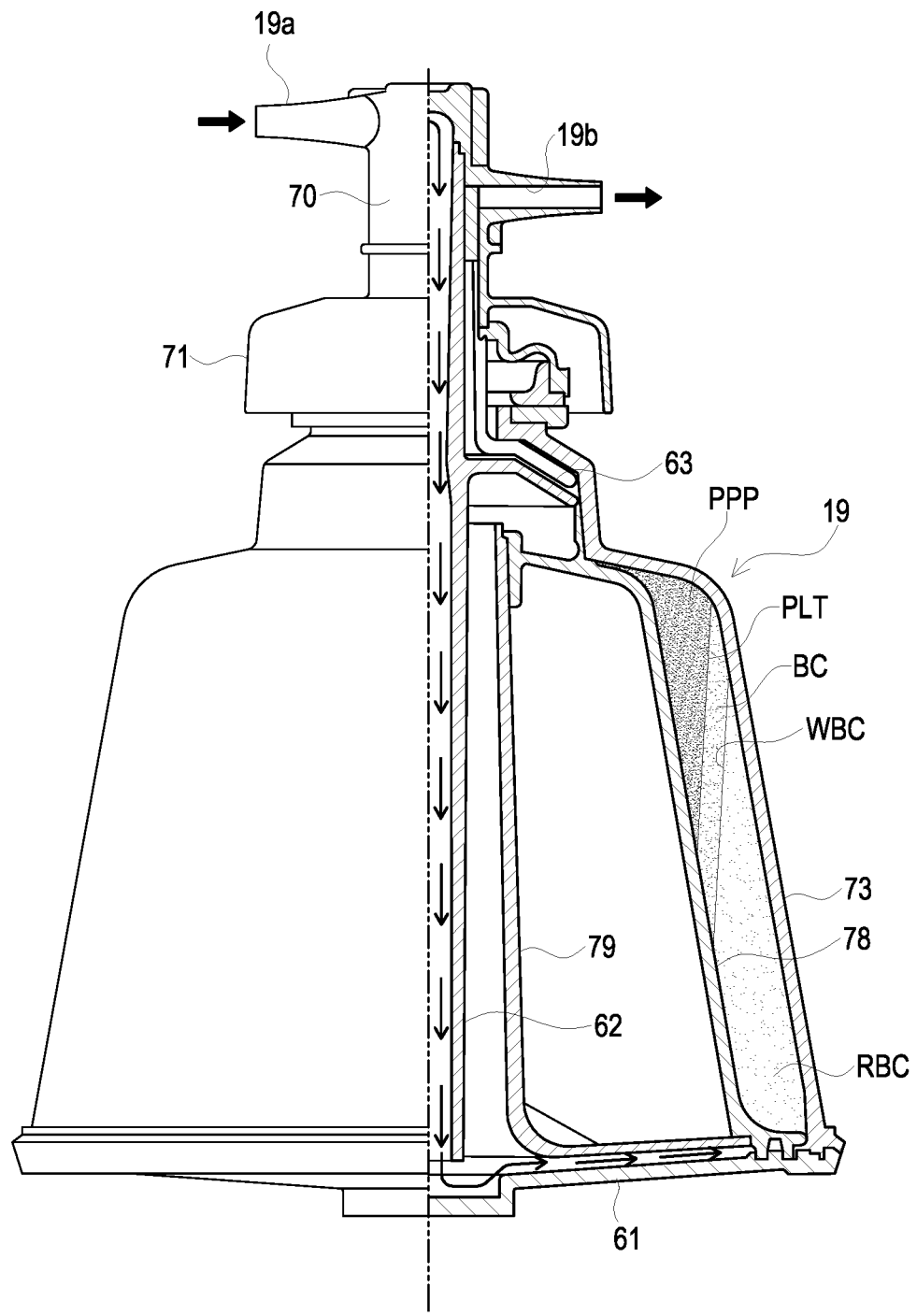
FIG. 14 illustrates a structure of a centrifuge bowl.

FIG. 14 illustrates a structure of a centrifuge bowl 19. The figure is divided by the center line, where the right hand side illustrates a cross sectional view and the left hand side illustrates an external view in dashed lines.

In the centrifuge bowl 19 in the blood component separation device, an inflow port 19a, and an outflow port 19b, are formed on the non-rotatable fixed portion 70. A cover 61 and a downwardly extending inflow tube 62 are coupled to the fixed portion 70. By these fixed portions, a side wall 73, an outer shell 78, an inner shell 79, and a bottom plate 60 are integrally and rotatably supported. The bottom plate 60 is coupled to the centrifuge bowl drive unit 15, for example, by suctioning so that the rotational force from the centrifuge bowl drive unit 15 can be transferred to the bottom plate 60. FIG. 14 illustrates a state where whole blood is supplied into the centrifuge bowl 19 from the inflow port 19a and separated into blood components by centrifugal force.

The centrifugal force produces layers of blood components in the space between the outer shell 78 and the side wall 73. These layers are, from outer side to inner side, in the descending order of specific gravity, a red blood cell layer RBC, a white blood cell layer WBC, a buffy coat layer BC, a platelet layer PLT, and a plasma layer PPP. It is difficult to separate the white blood cell layer WBC and the platelet layer PLT because values of specific gravity are close. Thus, the buffy coat layer BC including the white blood cell layer WBC and the platelet layer PLT exists. Typically, whole blood includes about 55% of plasma PPP, about 43.2% of red blood cells RBC, about 1.35% of white blood cells WBC, and 0.45% of platelets PLT.

The centrifuge bowl 19 has an outflow passage 63 in the inner periphery formed somewhat above the middle point of the inflow tube 62. So that the plasma layer PPP formed in the inner side of the space formed by the outer shell 78 and the side wall 73 first flows out from the centrifuge bowl 19 by passing through the outflow port 19b.

Figure 15:
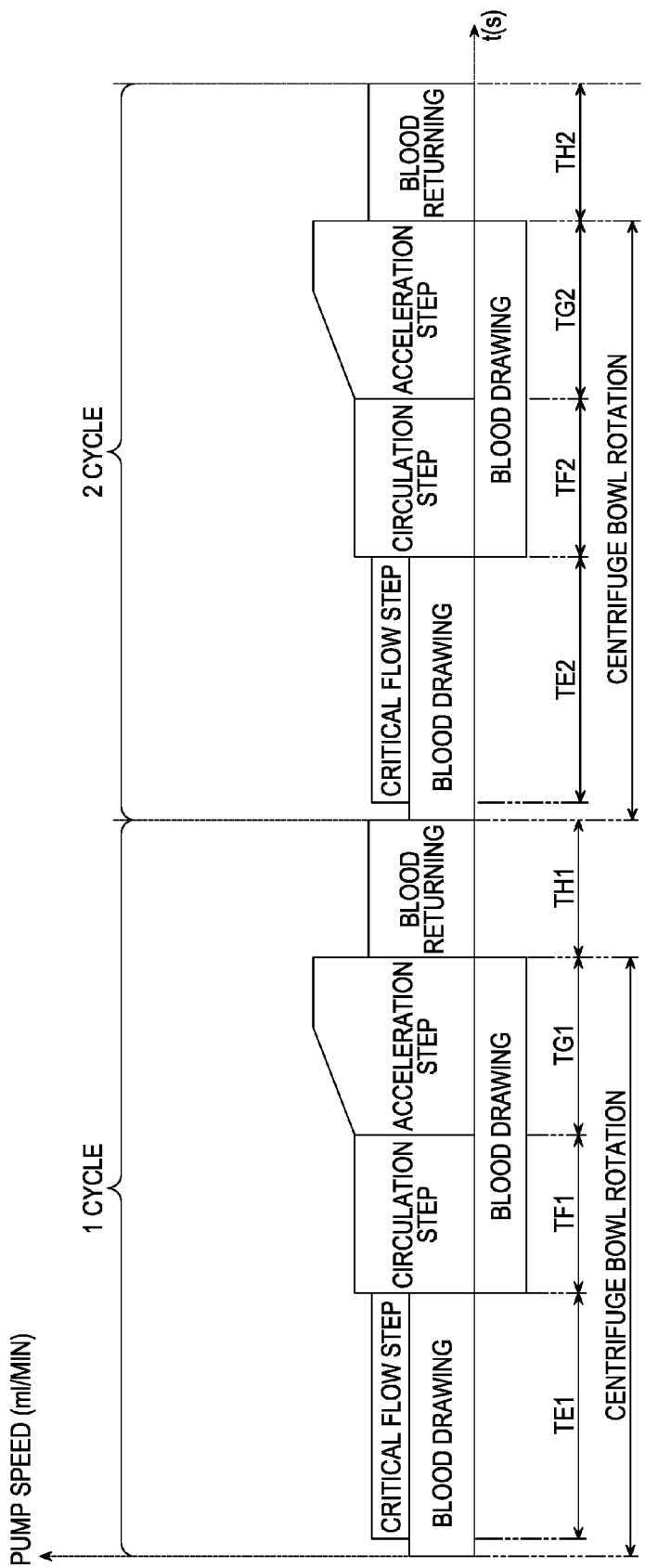
FIG. 15 illustrates operation of the blood component separation device in chronological order.

The operation of the blood component separation device configured as described above is shown in a flowchart in FIGS. 17 and 18. FIGS. 2 to 13 illustrate operations and steps of the blood component separation device. The object of the device is to collect high-concentration platelet liquid. FIG. 15 illustrates an operation chart showing the operation of the blood component separation device in chronological order.

FIG. 2 illustrates a first step. The pump outlined with a white inside shows that the pump is operating. The pump outlined with a black inside shows that the pump is not operating. The open/close valve outlined with a white inside shows that the valve is open. The open/close valve outlined with a black inside shows that the valve is closed.

Figure 17:
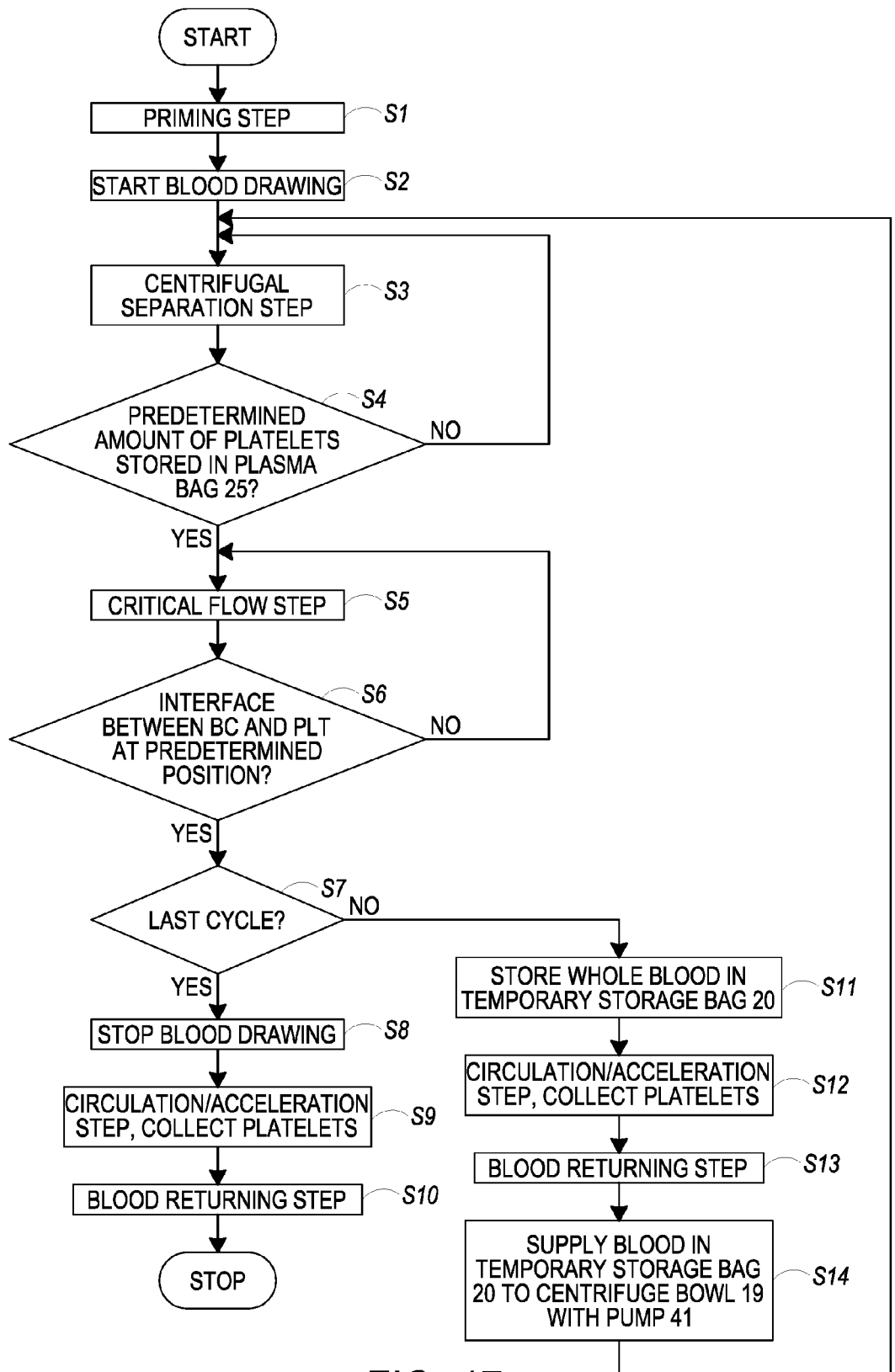
FIG. 17 is a flowchart showing the operation of the blood component separation device.

First, a priming step (S1) illustrated in FIG. 17 is performed. As illustrated in FIG. 2, the ACD pump 36 and the first blood pump 13 are driven to supply ACD liquid which prevents blood coagulation to the centrifuge bowl 19 via the opened first open/close valve 16, thereby performing the priming step (first step) of the centrifuge bowl 19, the first blood pump 13, etc. The priming step is performed to previously apply ACD liquid on portions in the donor tube 12, the first blood pump 13, the centrifuge bowl 19, etc., which are to make contact with blood, so that the blood will not coagulate when introduced. From the priming step, the centrifuge bowl drive unit 15 rotates the centrifuge bowl 19 at a predetermined rotational speed.

When the priming step (S1) is finished, the blood drawing needle 11 pierces a donor to start drawing of whole blood (S2). When the blood drawing needle 11 has pierced the donor, first, the initial blood flow is collected in the initial blood flow collecting bag 82 (see FIG. 1) provided in the initial blood flow collecting circuit 80. As illustrated in FIG. 1, the branch 87 provided on the donor tube 12 is initially configured to couple the blood drawing needle 11 and the initial blood flow collecting line 88. When a predetermined amount of blood is stored in the initial blood flow collecting bag 82, the initial blood flow collecting line 88 is choked by the klemme 90 to secure a flow passage, in the side of the first blood pump 13, of the donor tube 12.

The ACD pump 36 is driven again to supply ACD liquid to the donor tube 12 so as to be mixed with the whole blood which is supplied to the centrifuge bowl 19. When whole blood is supplied to the rotating centrifuge bowl 19, as illustrated in FIG. 2, the air (shown in dashed lines) inside the centrifuge bowl 19 is pushed by the plasma PPP to flow out from the outflow passage 63 (see FIG. 14) located in the inner periphery of the centrifuge bowl 19. The air flows through the opened fifth open/close valve 26 and is stored in the air bag 28.

In the centrifuge bowl 19, as illustrated in FIG. 14, the supplied whole blood is separated into components by the centrifugal force produced in the bowl.

Figure 3:
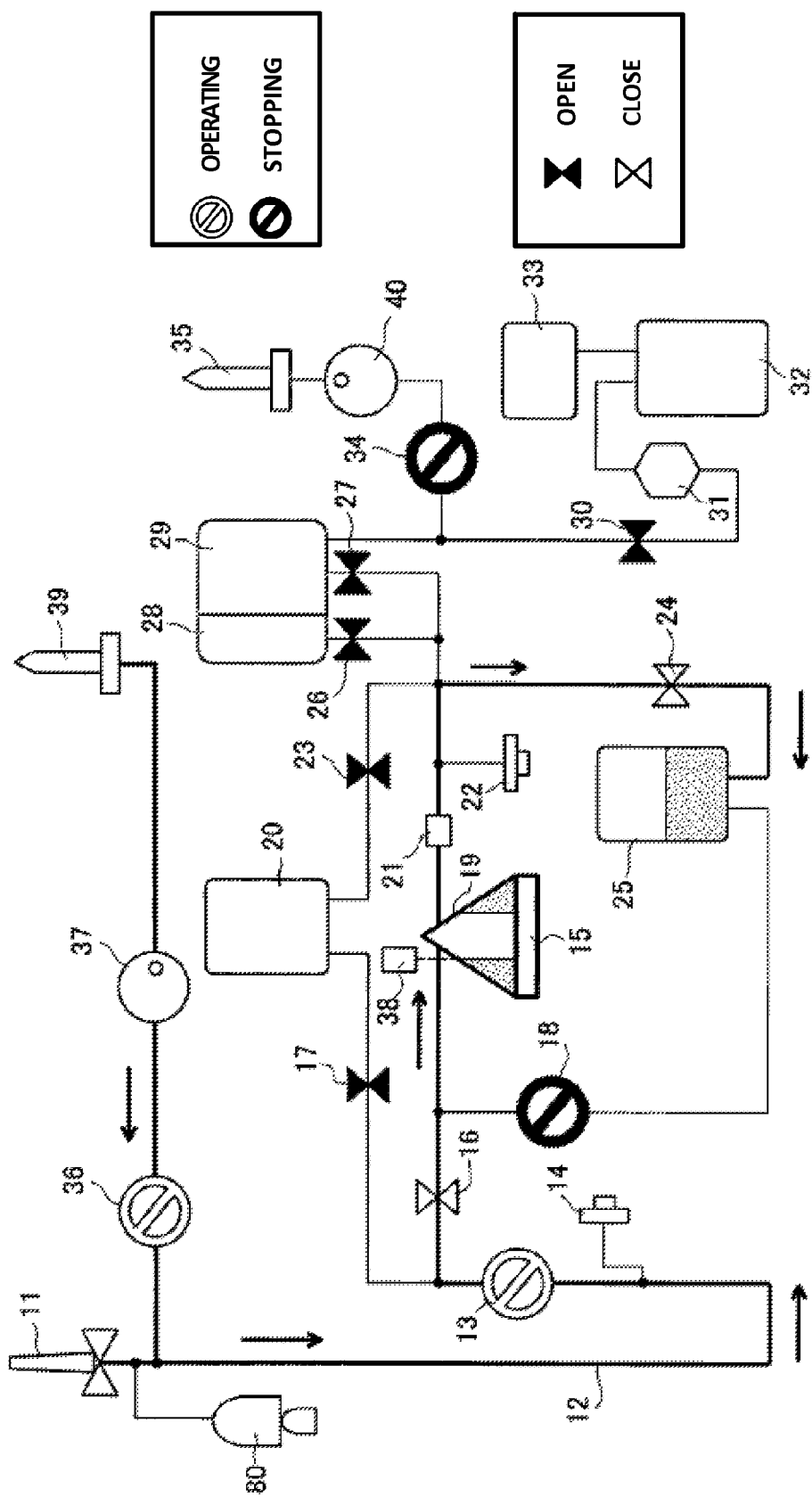
FIG. 3 illustrates a second step.

Then when the turbidity sensor 21 detects that the fluid flowing in the tube has changed from air to plasma PPP, the fifth open/close valve 26 is closed and the fourth open/close valve 24 is opened to store plasma PPP spilled out from the centrifuge bowl 19 in the plasma bag 25, as illustrated in FIG. 3. Thus the centrifugal separation step (S3) in FIG. 17 is performed. As illustrated in FIG. 14, only plasma PPP comes out first from the centrifuge bowl 19.

Figure 4:
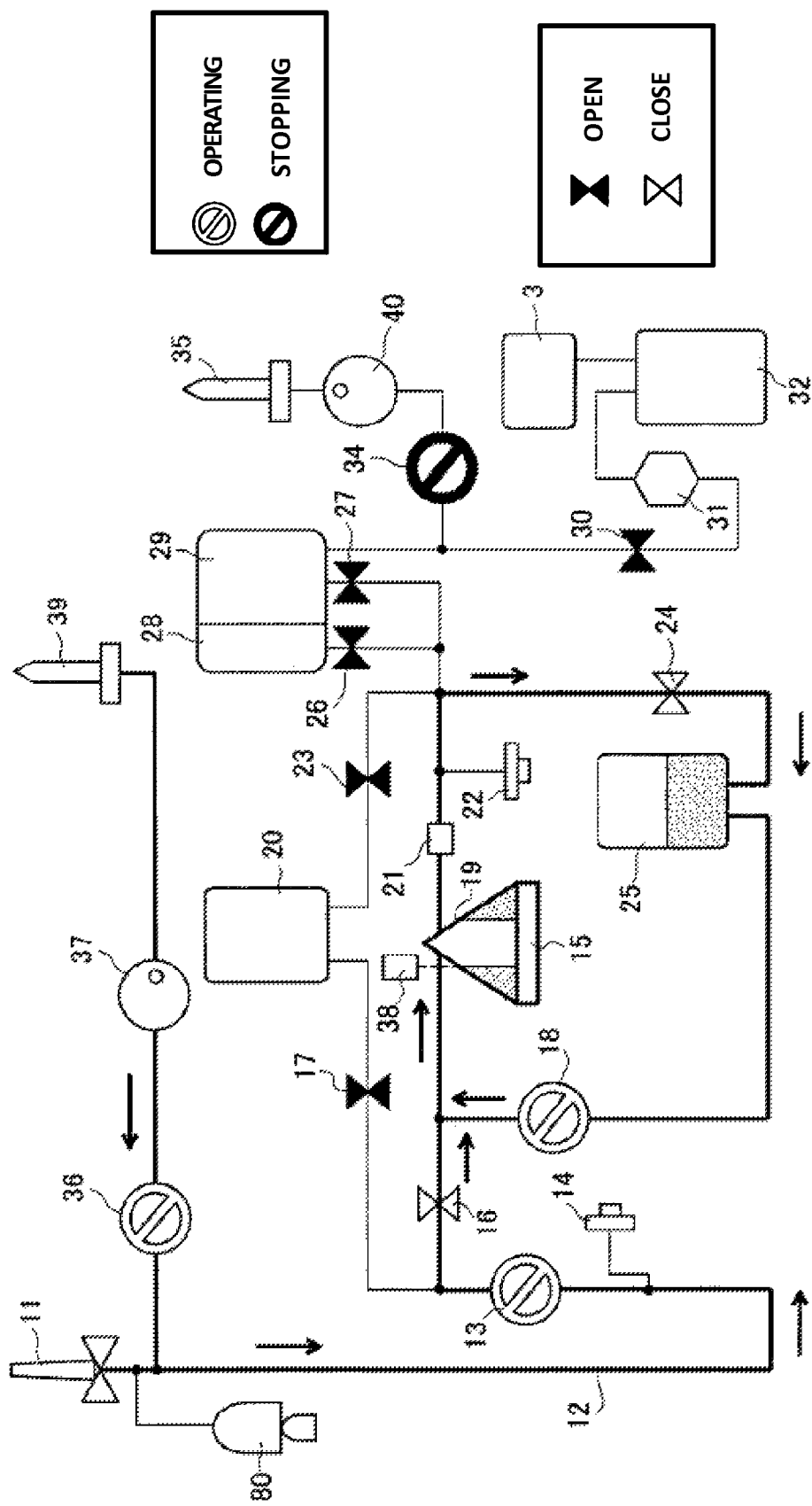
FIG. 4 illustrates a third step (critical flow step).

Then when a certain amount of plasma PPP (30 ml for the working example) is stored in the plasma bag 25 (S4: YES), the second blood pump 18 is driven to draw whole blood from the donor, mix the whole blood with the plasma PPP stored in the plasma bag 25, and supply the mixed whole blood and plasma PPP to the centrifuge bowl 19, as illustrated in FIG. 4 (S5). Thus, a third step (critical flow step) in FIG. 17 is performed. These are performed in a critical flow period TE shown in FIG. 15.

Figure 5:
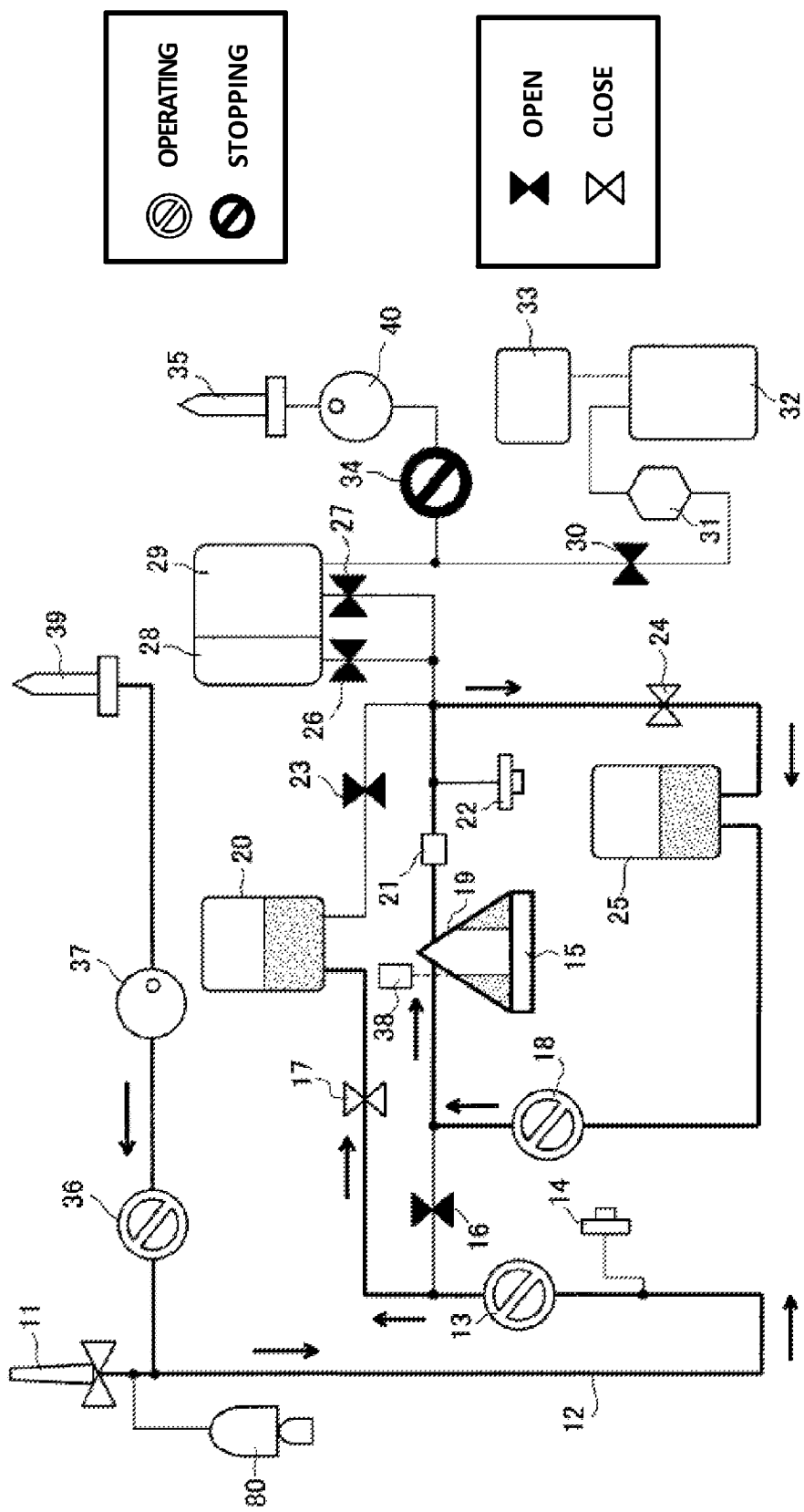
FIG. 5 illustrates a circulation step in a fourth step (circulation/acceleration step).

Then, when the interface sensor 38 detects that the interface between the buffy coat BC and the red blood cell RBC in FIG. 14 has come to a predetermined position (S6: YES), the first open/close valve 16 is closed with the second blood pump 18 driving as illustrated in FIG. 5. The plasma PPP in the plasma bag 25 then flows through the second blood pump 18, the centrifuge bowl 19, and the fourth open/close valve 24 to return back to the plasma bag 25, thereby performing a circulation step (fourth step) in the circulation/acceleration step. This is performed in a circulation period TF shown in FIG. 15.

At the same time, whether the present cycle is the last cycle is determined. When the present cycle is not the last cycle (S7: NO), the second open/close valve 17 is opened with the first blood pump 13 kept driving to store the drawn whole blood in the temporary storage bag 20 (S11). In other words, whole blood is kept drawn by storing the drawn whole blood in the temporary storage bag 20. Drawing of whole blood is continued until completion of the circulation/acceleration step or reaching a previously determined time or amount of drawing. In the last cycle (S7: YES), the first blood pump 13 is stopped to stop blood drawing (S8).

In the circulation step in the circulation/acceleration step of the working example, the circulation speed is set faster than the critical flow step so as that the plasma PPP circulates with the speed of 100 ml/min, flowing through the centrifuge bowl 19 within 30 to 40 seconds. In this manner, the concentration of particulates in the buffy coat layer BC in FIG. 14 decreases, whereby the white blood cell layer WBC having a larger specific gravity than platelets PLT deposits in the outer side of the buffy coat layer BC. That is, the platelet layer PLT and the white blood cell layer WBC can further distinctly be separated.

Figure 6:
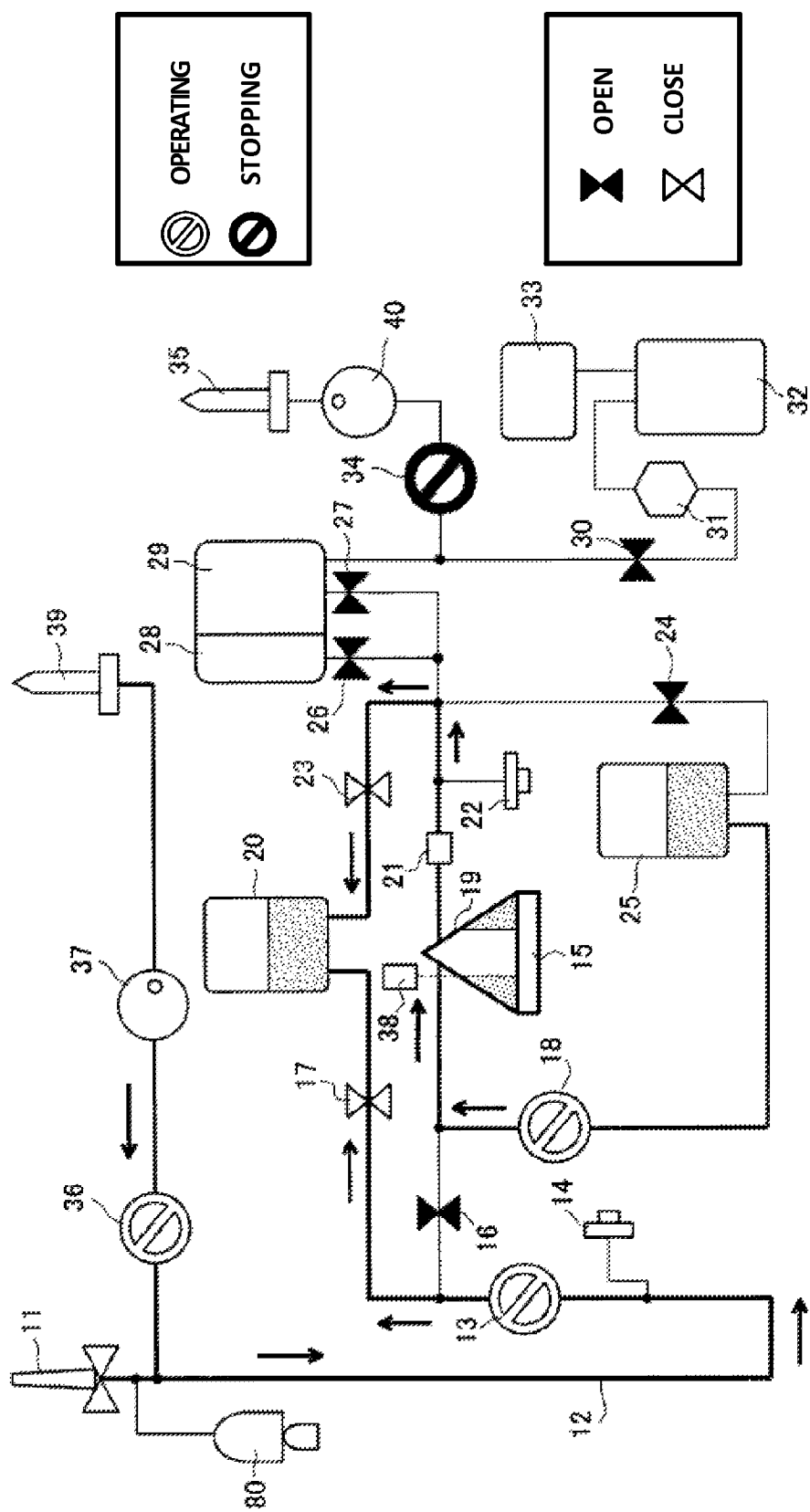
FIG. 6 illustrates a step for recovering low-concentration platelet liquid in a fifth step (circulation/acceleration step).

Then, after the circulation step is performed for a certain time period, an acceleration step (fifth step) in the circulation/acceleration step is performed as illustrated in FIG. 6. In the acceleration step, by controlling the rotational speed of the second blood pump 18, the rotational speed is gradually raised to gradually increase the flow rate of plasma PPP. In the working example, the flow rate starts from 100 ml/min and is raised to accelerate the flow rate of plasma PPP until platelets PLT flows out. This is performed in an acceleration period TG shown in FIG. 15. FIG. 17 describes the circulation step and the acceleration step together as the circulation/acceleration step (S9).

In the acceleration step, the platelets PLT receive ascending force and thereby flows out of the centrifuge bowl 19 from the outflow passage 63, as can be understood in FIG. 14. During this acceleration, the white blood cell layer WBC and the red blood cell layer RBC having large specific gravities, therefore receiving greater effect of centrifugal force, will not flow out from the outflow passage 63.

Figure 16:
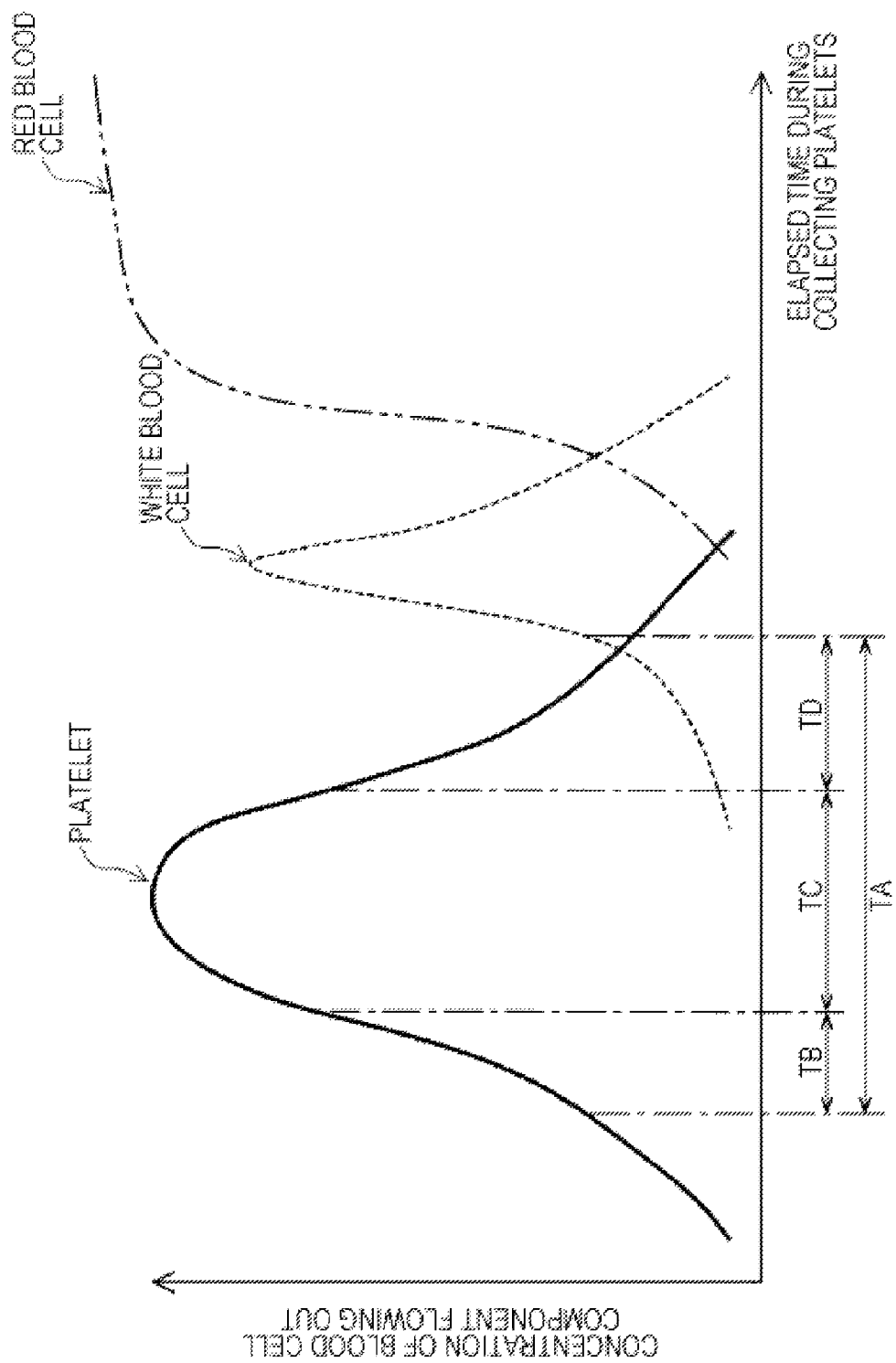
FIG. 16 illustrates change in concentrations of platelets, white blood cells, and red blood cells flowing out.

FIG. 16 illustrates change in concentrations of platelets PLT, white blood cells WBC, and red blood cells RBC flowing out. The horizontal axis represents elapsed time during collecting platelets PLT, and the vertical axis represents concentrations of blood cell components flowing out. First, platelets PLT flow out (outflow period TA). In this period, the outflow rate of platelets PLT gradually increases, and after peaking at the maximum flow rate, the outflow rate gradually decreases. Similarly, the outflow rate of white blood cells WBC gradually increases, and after peaking at the maximum flow rate, the outflow rate gradually decreases.

Figure 18:
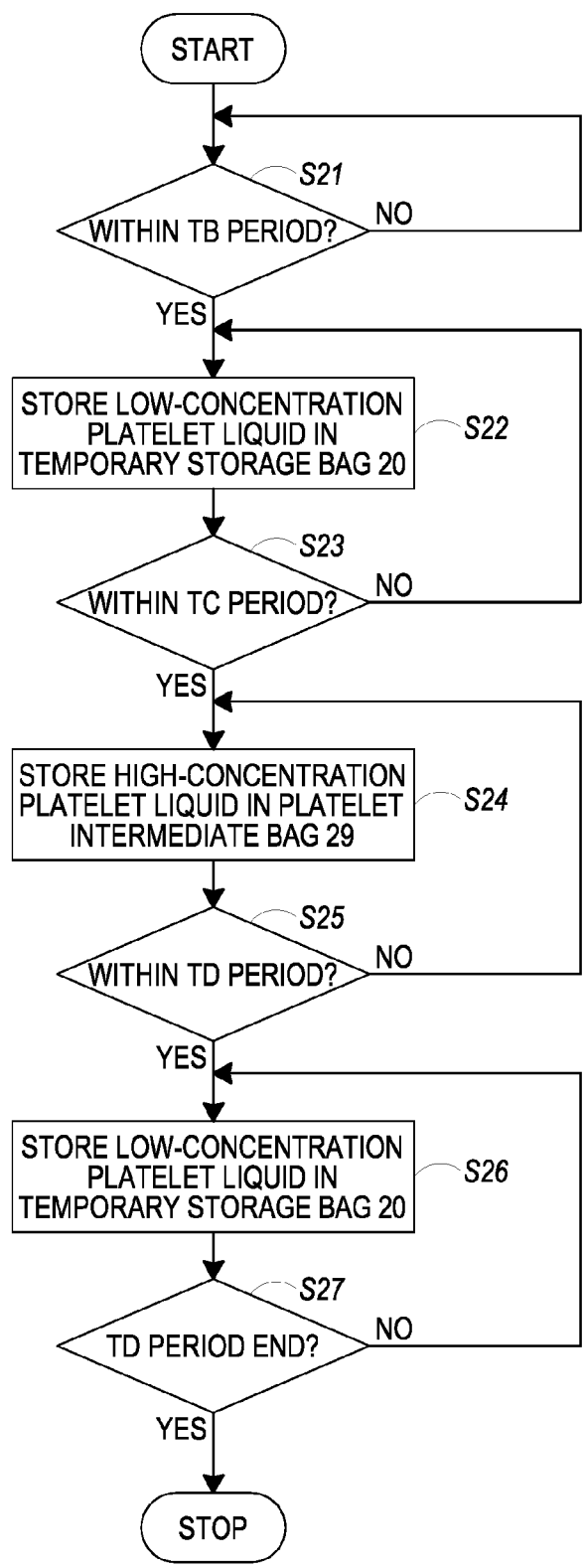
FIG. 18 is a flowchart showing operation performed in the collecting step of platelet liquid.

FIG. 18 illustrates S9, which is illustrated in FIG. 17, in detail in a flowchart showing the operation of the blood component separation device. The outflow period TA of platelets PLT can be divided in three periods, that is, a low-concentration period TB where low-concentration platelet liquid flows out at first, a high-concentration period TC, following the TB period, where high-concentration platelet liquid flows out, and a low-concentration period TD, following the TC period, where low-concentration platelet liquid flows out again. Low-concentration platelet liquid is not necessary for obtaining high-concentration platelet liquid.

In the working example, in the acceleration step as illustrated in FIG. 6, when the turbidity sensor 21 detects platelets PLT, that is, when it is determined that the present period is the period TB (S21: YES), the fourth open/close valve 24 is closed and the third open/close valve 23 is opened to store platelet liquid flowing out during the low-concentration period TB in FIG. 15 in the temporary storage bag 20 (S22). In this state, since the whole blood also flows into the temporary storage bag 20 to be stored, the low-concentration platelet liquid is stored in the temporary storage bag 20 mixed with the whole blood. Also in this state, the first blood pump 13 is kept driving so that the whole blood drawn from the donor is continuously stored in the temporary storage bag 20.

Note that, the temporary storage bag 20 is also used as a buffy coat bag as well as a whole blood bag.

Figure 7:
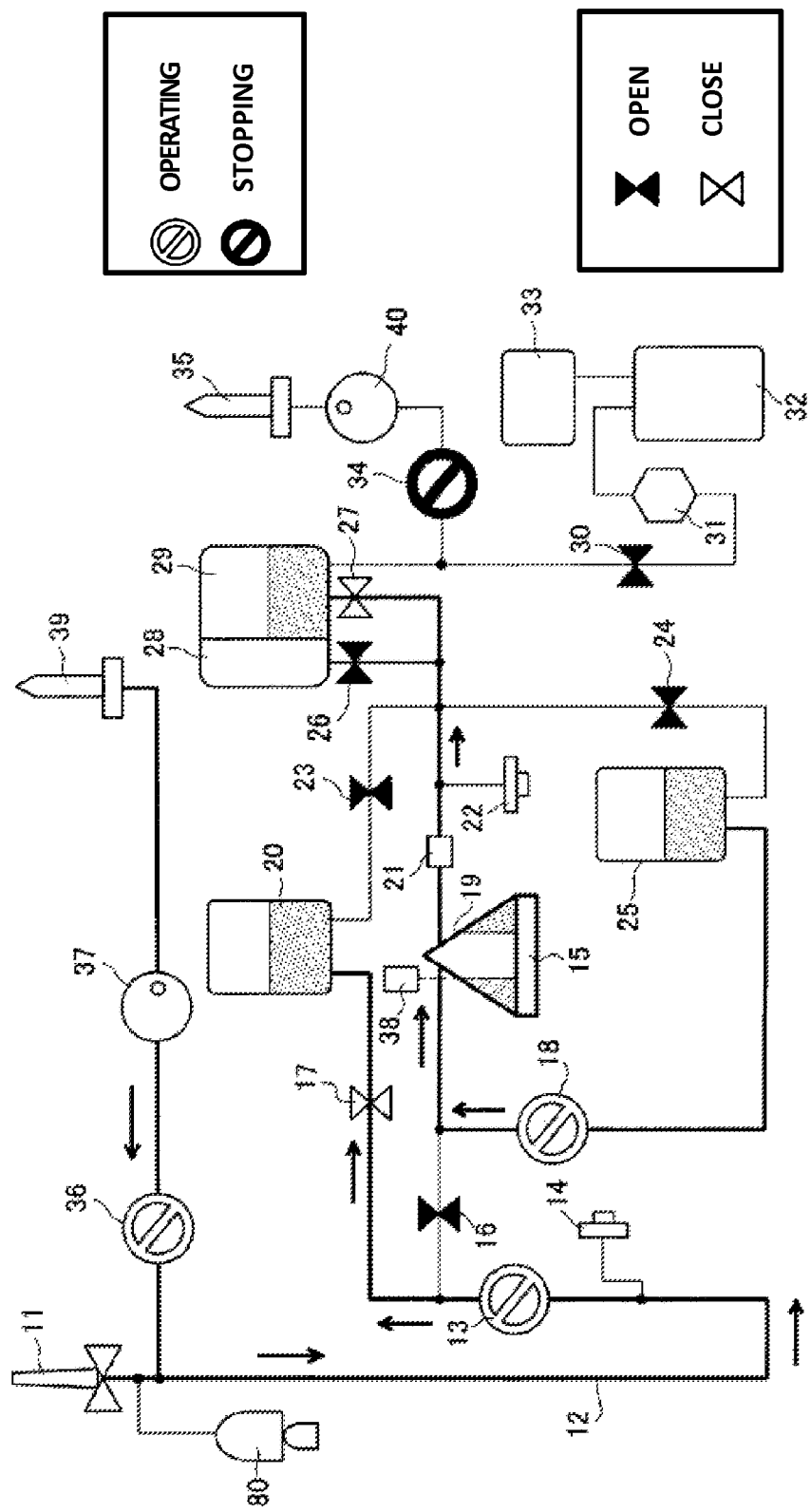
FIG. 7 illustrates a step for storing high-concentration platelet liquid in the fifth step (circulation/acceleration step).

When the turbidity sensor 21 detects that the concentration of platelet liquid is high, it is determined that the present period is the period TC (S23: YES), and the third open/close valve 23 is closed and the sixth open/close valve 27 is opened as illustrated in FIG. 7. In this manner, the high-concentration platelet liquid flowing out during the period TC can be stored in the platelet intermediate bag 29 (S24).

If the present cycle is not the last cycle (S7: NO), the first blood pump 13 is kept driving so that the whole blood drawn from the donor is continuously stored in the temporary storage bag 20.

Figure 8:
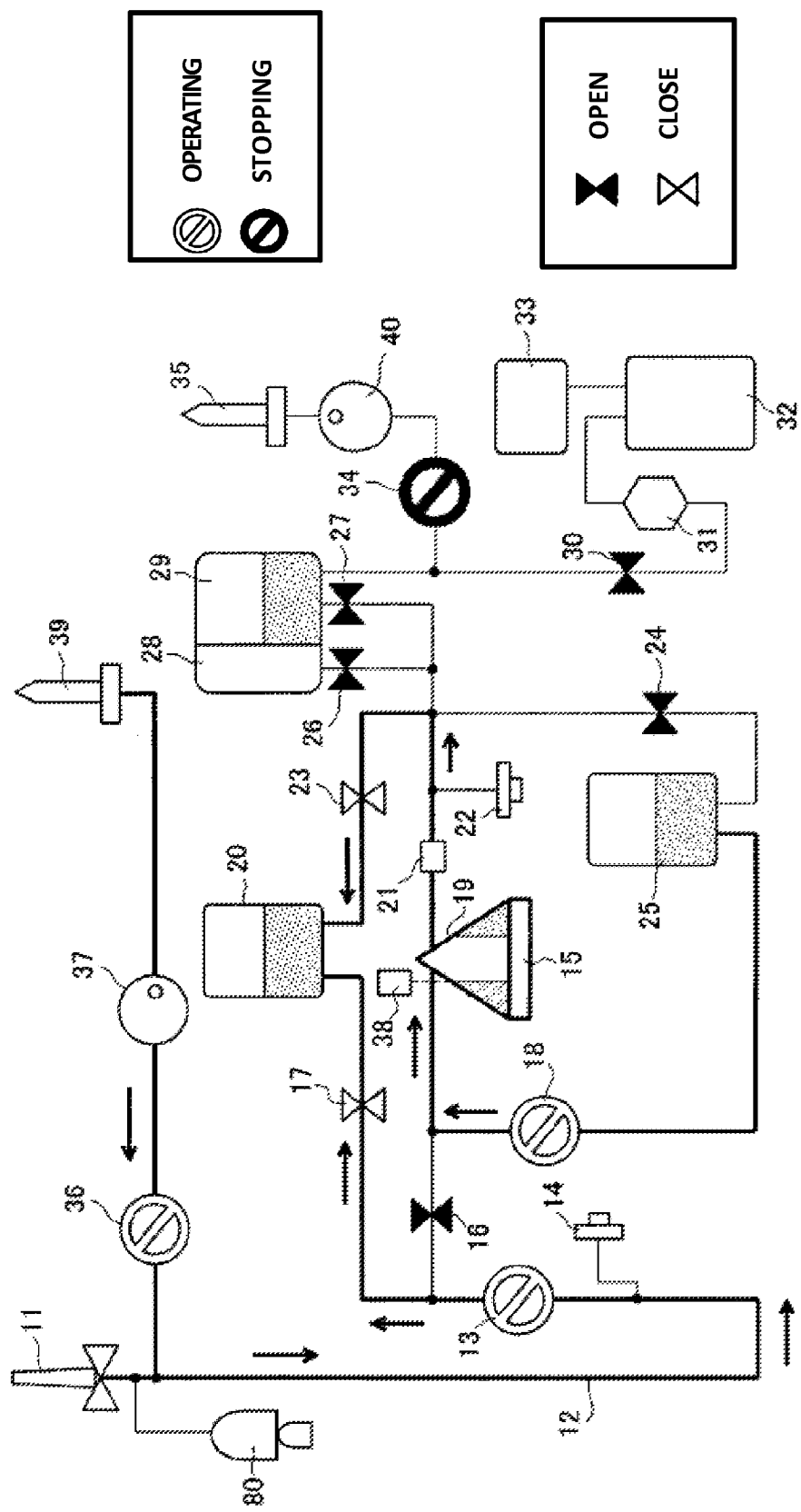
FIG. 8 illustrates a step for recovering low-concentration platelet liquid in the fifth step (circulation/acceleration step).

When the turbidity sensor 21 detects that the turbidity of platelets PLT is smaller than a predetermined value, it is determined that the present period is the period TD (S25: YES), and the sixth open/close valve 27 is closed and the third open/close valve 23 is opened as illustrated in FIG. 8. In this manner, the low-concentration platelet liquid flowing out during the period TD can be stored again in the temporary storage bag 20 (S26).

If the present cycle is not the last cycle (S7: NO), the first blood pump 13 is kept driving so that the whole blood drawn from the donor is continuously stored in the temporary storage bag 20.

When the turbidity of platelets PLT detected by the turbidity sensor 21 is smaller than the predetermined value, it is determined that the period TD is ended (S27: YES) and that the outflow of platelets PLT has finished. Then, the step proceeds to a blood returning step illustrated in FIGS. 9 and 17 (S10, S13).

Figure 9:
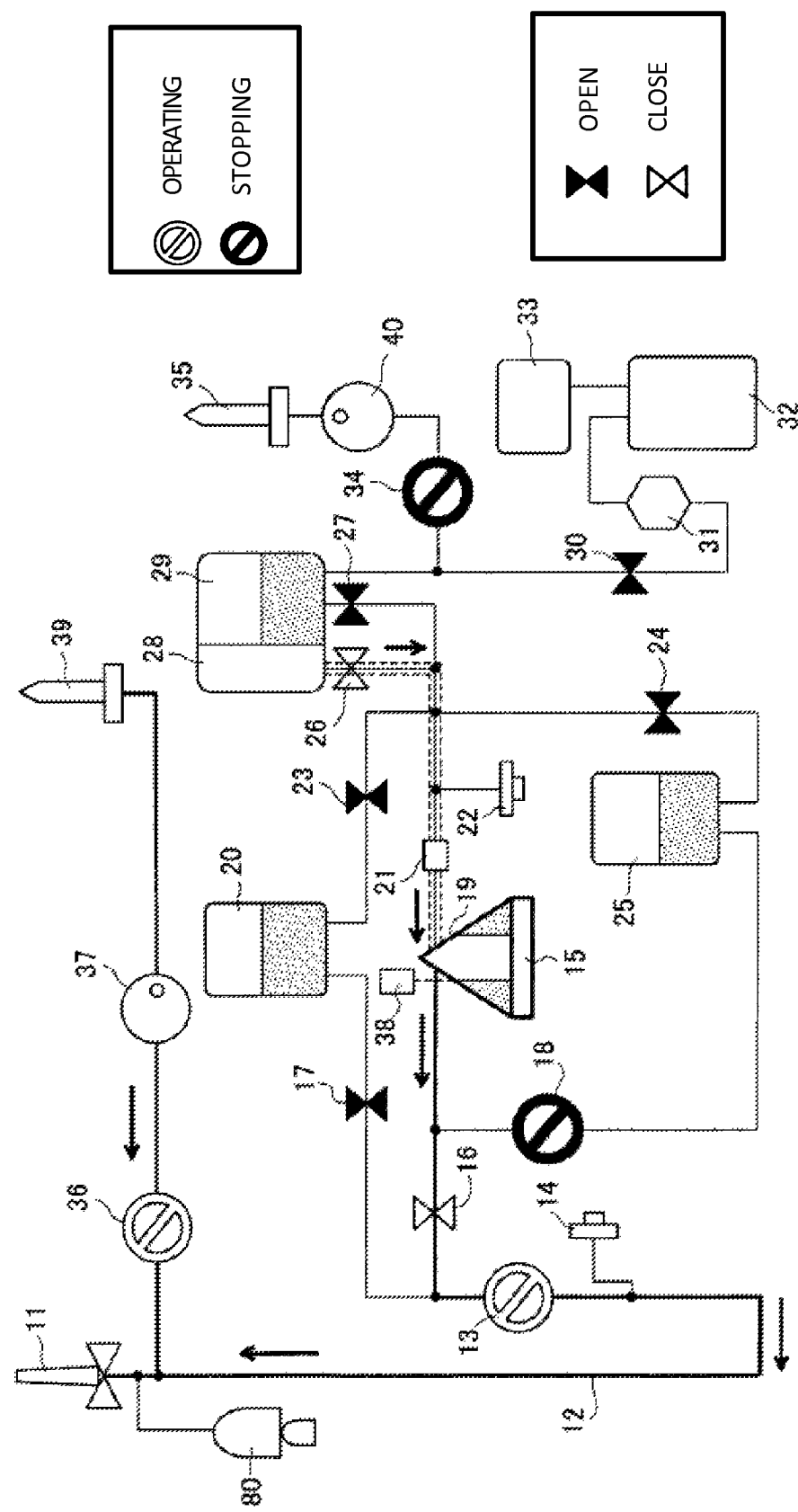
FIG. 9 illustrates a blood returning step.

That is, as illustrated in FIG. 9, the centrifuge bowl 19 stops rotation, the second open/close valve 17 and the third open/close valve 23 are closed, the first open/close valve 16 and the fifth open/close valve 26 are opened, and the first blood pump 13 is reversely rotated, whereby the blood returning starts to return the blood remaining in the centrifuge bowl 19 to the donor. The first blood pump 13 is reversely operated with double the rotational speed of the normal rotation to shorten the time of blood returning. The air (illustrated in dashed lines) stored in the air bag 28 flows into the centrifuge bowl 19 via the opened fifth open/close valve 26 to return the blood remaining in the centrifuge bowl 19 to the donor.

Further, when required, the second blood pump 18 is driven to return the excessive plasma PPP stored in the plasma bag 25.

Figure 10:
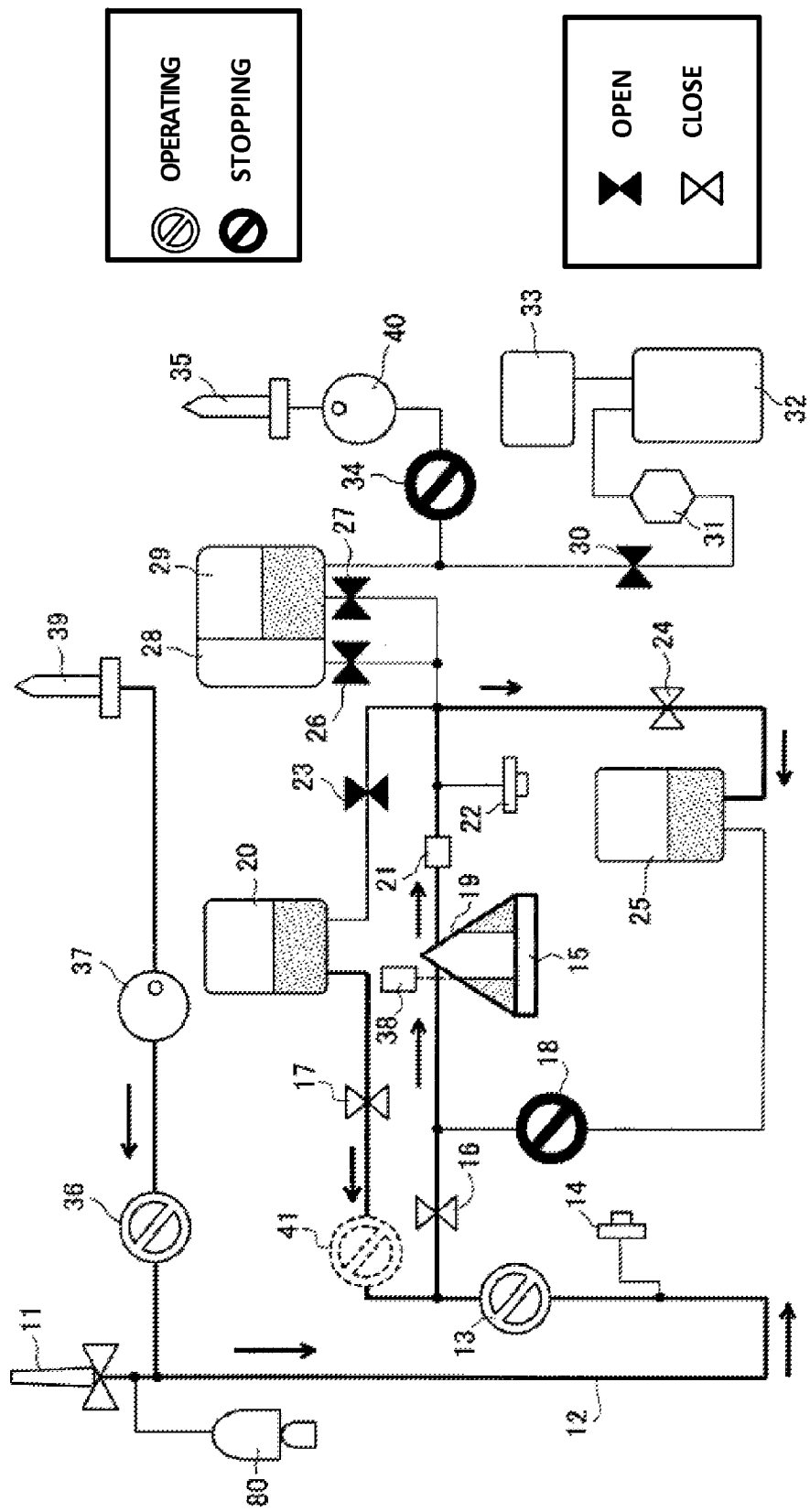
FIG. 10 illustrates the second step in a second cycle.

When the blood returning finishes, and if the present cycle is the last cycle (S7: YES), the entire step is finished. When the present cycle is not the last cycle (S7: NO), the centrifuge bowl 19 starts rotating as illustrated in FIG. 10 and the first blood pump 13 starts normal rotation again to perform blood drawing. At the same time, the second open/close valve 17 is opened to allow the blood stored in the temporary storage bag 20 to flow into the centrifuge bowl 19 (S14). The liquid supply from the temporary storage bag 20 may be performed by difference in elevation or by providing a blood pump 41 (illustrated in a dashed line) between the second open/close valve 17 and the first open/close valve 16 as illustrated in FIG. 10. When blood is supplied again to the centrifuge bowl 19, the air in the centrifuge bowl 19 is stored in the air bag 28 via the opened fifth open/close valve 26, which is not illustrated since the state is similar to the state illustrated in FIG. 2. When the turbidity sensor 21 detects that the fluid flowing in the tube has changed from air to plasma PPP, the fifth open/close valve 26 is closed and the fourth open/close valve 24 is opened to store the plasma PPP spilled out from the centrifuge bowl 19 in the plasma bag 25 (S3).

Figure 11:
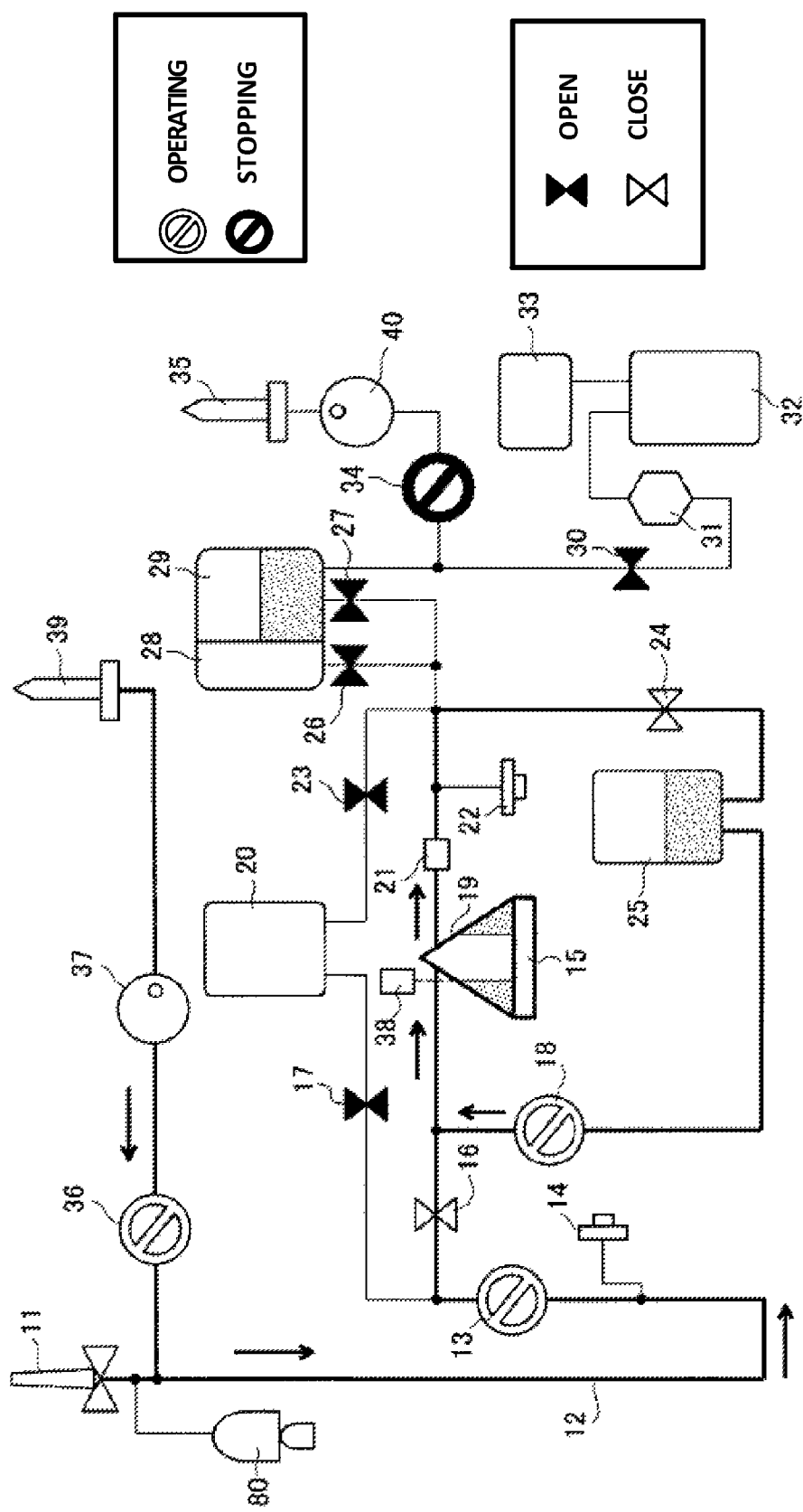
FIG. 11 illustrates the second step in a third cycle.

Then, when it is confirmed that all the blood in the temporary storage bag 20 has returned to the centrifuge bowl 19 and that a predetermined amount of plasma PPP is stored in the plasma bag 25 (S4: YES), as illustrated in FIG. 11 (state same as in FIG. 4), the second open/close valve 17 is closed and the second blood pump 18 is driven to start the critical flow step of plasma PPP. The step is followed by the step in FIG. 5 (circulation step).

This cycle is repeated, typically three or four times, until a predetermined amount of platelets PLT is obtained. For example, when the operation finishes with three cycles, blood drawing is performed in parallel in a circulation period TF2 and an acceleration period TG2 in the second cycle to store whole blood in the temporary storage bag 20. Then during blood drawing in the third cycle, the blood in the temporary storage bag 20 is mixed with whole blood and supplied to the centrifuge bowl 19. Further, in a circulation period TF3 and an acceleration period TG3 in the third cycle, blood drawing is not performed. This is because the fourth cycle will not be performed.

When the operation finishes with three cycles, the blood drawing needle 11 is removed from the donor after blood returning in the third cycle finishes, and the blood drawing finishes.

Figure 12:
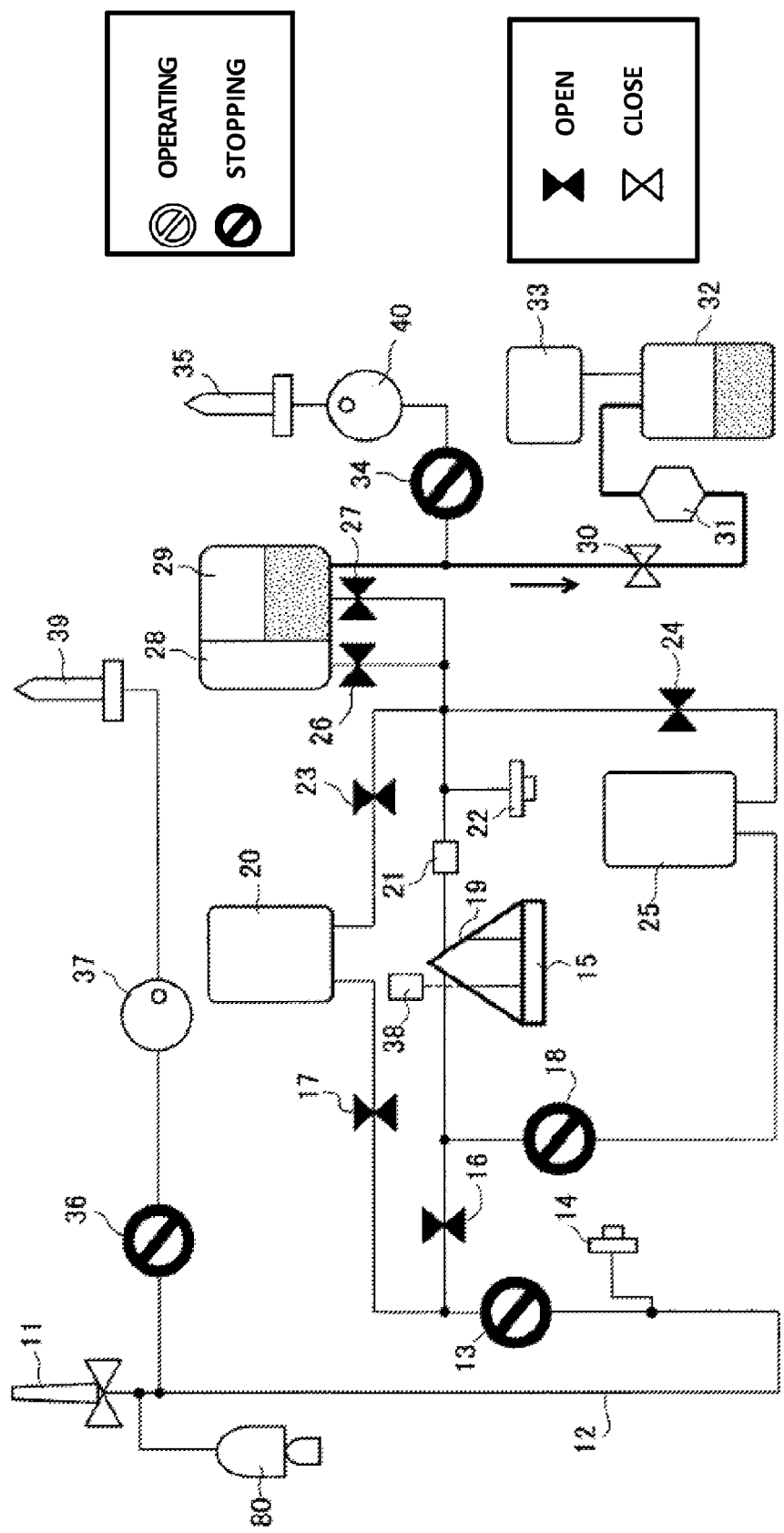
FIG. 12 illustrates a processing step of platelet liquid.

Then, the third blood pump 34 is driven to inject a suitable amount of platelet reserve liquid into the platelet intermediate bag 29 from a bottle needle 35 coupled to the platelet reserve liquid bottle (not shown). Further, as illustrated in FIG. 12, the seventh open/close valve 30 is opened to inject high-concentration platelet liquid stored in the platelet intermediate bag 29 into the platelet bag 32 through the white blood cell removal filter 31. In this process, the air in the platelet bag 32 moves into the air bag 33.

Figure 13:
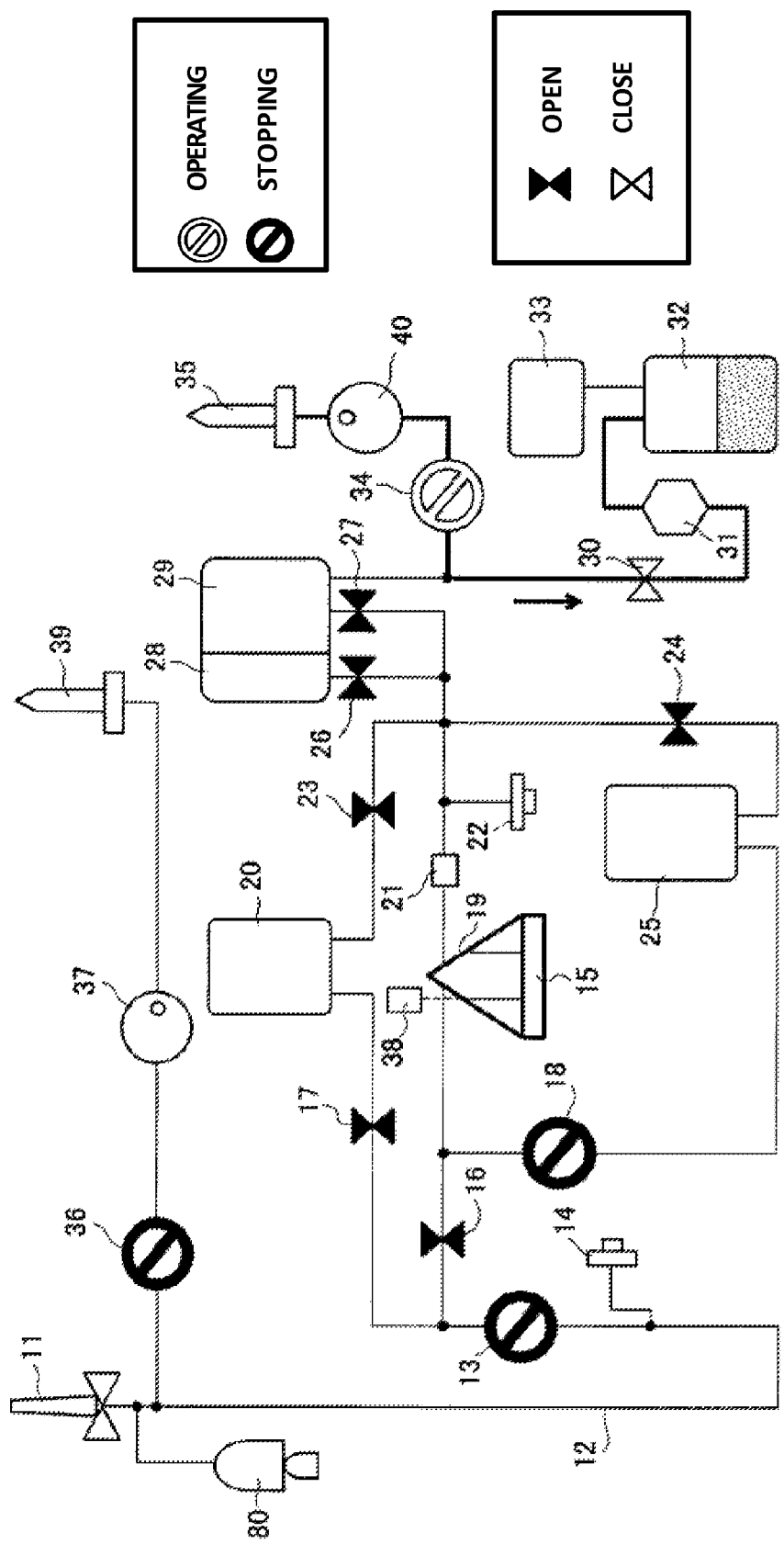
FIG. 13 illustrates a final processing step of platelet liquid.

After confirming that the high-concentration platelet liquid stored in the platelet intermediate bag 29 has completely been taken out, the third blood pump 34 is driven to inject the platelet reserve liquid remaining in the platelet reserve liquid bottle into the platelet bag 32, through the sterilizing filter 40 and the white blood cell removal filter 31, from the bottle needle 35 coupled to the platelet reserve liquid bottle, as illustrated in FIG. 13. In this manner, the high-concentration platelet liquid which is already filtered and remaining on the white blood cell removal filter 31 is recovered. Then, two tubes of the platelet bag 32 is sealed. In this manner, the platelet bag 32 storing high-concentration platelet liquid is provided.

As described above in detail, the blood component separation device according to the embodiment includes (1) a centrifuge bowl 19 (centrifugal separator) for separating a predetermined blood component from blood and containers (the plasma bag 25 and the platelet intermediate bag 29) for containing the predetermined blood component which is centrifugally separated. The blood component separation device is configured to perform (a) centrifugal separation step for introducing whole blood drawn from a donor into the centrifuge bowl 19 to separate the whole blood into a plurality of blood components, (b) critical flow step (circulation flow step in the present invention) for introducing plasma PPP (first blood component), among centrifugally separated blood components, into the centrifuge bowl 19 together with whole blood, and (c) circulation/acceleration step, performed after separating the plasma PPP in the critical flow step, in which only the plasma PPP is introduced into the centrifuge bowl 19 to further circulate the plasma PPP for a predetermined period of time, and platelets PLT (second blood component) is separated in the centrifuge bowl 19 to be collected by increasing the circulation speed. The blood component separation device is characterized in that the whole blood collected from a donor is temporarily stored in the temporary storage bag 20 (temporary storage container) during at least a time period in the circulation/acceleration step. (2) The blood component separation device described in (1) is preferably configured to perform (d) blood returning step for returning blood components, remaining after collecting platelets PLT in the circulation/acceleration step, to the donor. The blood component separation device is characterized in that the whole blood stored in the temporary storage bag 20 (temporary storage container) is introduced in the centrifuge bowl 19 together with the whole blood collected in the centrifugal separation step in the following cycle, where the steps (a) to (d) constitute one cycle. This allows drawing whole blood from the donor in parallel with performing circulation/acceleration step in a first cycle (present cycle), so that the time required for drawing whole blood in a second cycle (following cycle) can be reduced, thereby reducing the time required for the entire process. This reduces the time to keep the donor for blood drawing.

For example, typical time periods in each cycle are about 12 minutes for blood drawing (centrifugal separation step and critical flow step), about 30 to 40 seconds for the circulation step in the circulation/acceleration step, about 20 to 30 seconds for the acceleration step in the circulation/acceleration step, and about 5 minutes for blood returning. According to the present invention, since blood is previously drawn for about one minute in the first cycle, the time required for drawing blood in the second cycle can be reduced by one minute, that is, to about eleven minutes. Similarly, when total three cycles are performed, the time required for drawing blood in the third cycle can be reduced by one minute, that is, to about eleven minutes.

There is a problem for a donor that the amount of blood circulating outside the body increases, although it may not be a problem for 90% of donors. If the result of previous check shows that there may be a problem in increasing the amount of blood circulating outside the body, a switching unit may be used to avoid drawing whole blood in parallel with the circulation/acceleration step in the first cycle (present cycle), and to draw whole blood in the second cycle (following cycle) after returning blood.

It goes without saying that, in the last cycle, whole blood is not drawn for the following cycle because there is no cycle following the last cycle.

(3) In the blood component separation device according to (1) or (2), the circulation/acceleration step includes a first collecting step for transferring a low-concentration portion of the platelet liquid (low-concentration second blood component) to the temporary storage bag 20 and a second collecting step for collecting a high-concentration portion of the second blood component (high-concentration second blood component). The blood component separation device is characterized in that the low-concentration platelet liquid transferred to the temporary storage bag 20 is introduced into the centrifuge bowl 19 together with the whole blood collected in the temporary storage bag 20 in the following cycle and the whole blood drawn in the following cycle. Thus, the blood component separation device can be applied to the BC cycle for obtaining high-concentration platelets PLT allowing drawing whole blood from a donor in parallel with performing the circulation/acceleration step in the first cycle (present cycle). This reduces the time required for drawing whole blood in the second cycle (following cycle) and the time required for the entire process, thereby reducing the time to keep the donor for blood drawing.

(4) The blood component separation device according to (1) or (2) further includes the blood pump 41 for introducing at least either of the whole blood and the low-concentration platelet liquid stored in the temporary storage bag 20 in the preceding cycle into the centrifuge bowl 19 in the centrifugal separation step in the following cycle. Therefore, at least either of the whole blood and the low-concentration platelet liquid stored in the preceding cycle can quickly and surely be introduced into the centrifuge bowl 19.

(5) The blood component separation device according to (3) includes a second storage container for temporarily storing the low-concentration platelet liquid in the circulation/acceleration step. The blood component separation device is characterized in that the second storage container is also used as the temporary storage bag 20, so that there is no need to additionally provide a second storage container which makes the apparatus large nor to prepare a disposable second storage container, thereby reducing cost.

The specific exemplary embodiment of the present invention is described above in detail. The present invention is not limited to such exemplary embodiment and various applications can be made.

For example, unlike the exemplary embodiment providing the temporary storage bag 20 used as both the buffy coat bag and the whole blood bag, the buffy coat bag and the whole blood bag may separately be provided in parallel.

Unlike the exemplary embodiment drawing whole blood in parallel throughout the entire period of the circulation/acceleration step, whole blood may be drawn in parallel during a portion of the entire period.

In the present embodiment, drawing of whole blood is performed in parallel with the circulation/acceleration step. However, a switching unit may be provided in the blood component separation device to perform drawing of whole blood not in parallel, as is performed in conventional technique.

REFERENCE SIGNS LIST 15 centrifuge bowl drive unit
19 centrifuge bowl (centrifugal separator)
20 temporary storage bag (second container)
21 turbidity sensor
25 plasma bag (first container)
28, 33 air bag
29 platelet intermediate bag (third container)
32 platelet bag
38 interface sensor
PPP plasma (first blood component)
PLT platelet (second blood component)
WBC white blood cell
BC buffy coat
RBC red blood cell

The invention claimed is:

1. A method for controlling a blood component separation device comprising a centrifugal separator and configured to separate a predetermined blood component from blood, said method comprising cycles of steps (a) through (d)
   (a) a centrifugal separation step introducing whole blood drawn from a donor into the centrifugal separator to separate the whole blood into a plurality of blood components and temporarily storing at least part of a first separated blood component in a temporary storage container,
   (b) a critical flow step introducing said first separated blood component into the centrifugal separator together with whole blood, and
   (c) a circulation/acceleration step, preformed after a predetermined amount of the first separated blood component is separated in the critical flow step, in which
      (1) supply of whole blood to the centrifugal separator is stopped;
      (2) the first separated blood component is introduced into the centrifugal separator to further circulate the first separated blood component for a predetermined period of time, and a second blood component to be collected is separated by the centrifugal separator by increasing a circulation speed,
      (3) whole blood being collected from the donor during the circulation/acceleration step is temporarily stored in said temporary storage container during at least a time period in the circulation/acceleration step, and
      (4) collecting at least some of the second blood component, and
   (d) a blood returning step for returning to the donor blood components remaining after collecting at least some of the second component,
   wherein in at least some cycles the whole blood drawn from the donor in step (a) comprises the whole blood transferred to the temporary storage in a previous cycle and whole blood drawn from the donor in the current cycle.

2. The method according to claim 1 wherein said part of the first separated blood component is plasma and said plasma and whole blood are simultaneously flowed into said temporary storage container during said circulation-acceleration step.

3. The method according to claim 2 wherein said plasma is transferred through a plasma bag from an outlet of said centrifugal separator to an inlet of said centrifugal separator.

* * * * *